US012426783B2

(12) United States Patent
Toth et al.

(10) Patent No.: US 12,426,783 B2
(45) Date of Patent: Sep. 30, 2025

(54) GATEWAY DEVICE FACILITATING COLLECTION AND MANAGEMENT OF DATA FROM A BODY AREA NETWORK TO A STUDY COORDINATING SYSTEM

(71) Applicant: LifeLens Technologies, Inc., Ivyland, PA (US)

(72) Inventors: Landy Toth, Doylestown, PA (US); Robert S. Schwartz, Inver Grove Heights, MN (US); Dhananjai Hariharan, Doylestown, PA (US)

(73) Assignee: LifeLens Technologies, Inc., Ivyland, PA (US)

( * ) Notice: Subject to any disclaimer, the term of this patent is extended or adjusted under 35 U.S.C. 154(b) by 131 days.

(21) Appl. No.: 17/927,033

(22) PCT Filed: May 20, 2021

(86) PCT No.: PCT/US2021/033441
§ 371 (c)(1),
(2) Date: Nov. 22, 2022

(87) PCT Pub. No.: WO2021/236948
PCT Pub. Date: Nov. 25, 2021

(65) Prior Publication Data
US 2023/0200649 A1    Jun. 29, 2023

Related U.S. Application Data

(60) Provisional application No. 63/029,091, filed on May 22, 2020.

(51) Int. Cl.
*A61B 5/00* (2006.01)
*G16H 40/67* (2018.01)

(52) U.S. Cl.
CPC .......... *A61B 5/0024* (2013.01); *A61B 5/0022* (2013.01); *G16H 40/67* (2018.01)

(58) Field of Classification Search
CPC ..... A61B 5/0024; A61B 5/0022; G16H 40/67
See application file for complete search history.

(56) References Cited

U.S. PATENT DOCUMENTS 7,904,133 B2 *  3/2011  Gehman .............. A61B 5/0006
                                                    600/509
2012/0094600 A1 *  4/2012  DelloStritto ............. H04Q 9/00
                                                    455/41.2

(Continued)

FOREIGN PATENT DOCUMENTS

EP        3400056 B1    5/2020
WO     2014197822 A2   12/2014

(Continued)

OTHER PUBLICATIONS

V. G. T. N. Vidanagama, D. Arai and T. Ogishi, "Service Environment for Smart Wireless Devices: An M2M Gateway Selection Scheme," in IEEE Access, vol. 3, pp. 666-677, 2015, doi: 10.1109/ACCESS.2015.2436907. (Year: 2015).*

(Continued)

*Primary Examiner* — Sun M Li
(74) *Attorney, Agent, or Firm* — Ryan, Mason & Lewis, LLP

(57) ABSTRACT

A gateway device comprises a processing device, network interface, and sensor device interconnect. The processing device is configured to pair sensor devices associated with a subject with the gateway device utilizing the sensor device interconnect, wherein pairing the sensor devices comprises identifying sensing capabilities of the sensor devices. The processing device is also configured to provide, to a study coordinating system over a first network connection established utilizing the network interface, a gateway identifier (Continued)

and information characterizing the identified sensing capabilities of the sensor devices paired with the gateway device. The processing device is further configured to receive, from the study coordinating system, parameters for a study identifying data to be collected from sensor devices paired with the gateway device, to collect the identified data from the sensor devices over a second network connection established utilizing the network interface, and to provide the collected data to the study coordinating system.

20 Claims, 12 Drawing Sheets

(56) References Cited

U.S. PATENT DOCUMENTS

| | | |
|---|---|---|
| 2012/0232398 A1 | 9/2012 | Roham et al. |
| 2013/0023214 A1 | 1/2013 | Wang et al. |
| 2014/0089007 A1* | 3/2014 | Sim ................. G16H 10/60 705/2 |
| 2014/0106673 A1 | 4/2014 | Son et al. |
| 2014/0341584 A1* | 11/2014 | Hopewell .......... H04B 10/50 398/104 |
| 2015/0050888 A1* | 2/2015 | Baker ................ H04W 74/02 455/41.2 |
| 2015/0190053 A1* | 7/2015 | Baker ................. A61B 5/7425 340/870.3 |
| 2016/0267238 A1 | 9/2016 | Nag |
| 2017/0134884 A1* | 5/2017 | Taborn ................. H04B 5/72 |
| 2017/0372024 A1 | 12/2017 | Ikonen et al. |
| 2018/0001184 A1* | 1/2018 | Tran ..................... G16H 50/20 |
| 2020/0251213 A1* | 8/2020 | Tran ..................... G06N 20/00 |

FOREIGN PATENT DOCUMENTS

| | | | |
|---|---|---|---|
| WO | 2016019250 A1 | 2/2016 | |
| WO | 2017190049 A1 | 11/2017 | |
| WO | WO-2019023055 A1 * | 1/2019 | ........... A61B 5/0022 |

OTHER PUBLICATIONS

Darwish A, Hassanien AE. Wearable and implantable wireless sensor network solutions for healthcare monitoring. Sensors (Basel). 2011;11(6):5561-95. doi: 10.3390/s110605561. Epub May 26, 2011. (Year: 2011).*

R. K. Mishra and R. Pandey, "Aspects of Network Architecture for Remote Healthcare Systems," 2016 2nd International Conference on Computational Intelligence and Networks (CINE), Bhubaneswar, India, 2016, pp. 47-53, doi: 10.1109/CINE.2016.16. (Year: 2016).*

Islam et al., 2015, The internet of things for health care: a comprehensive survey (Year: 2015).*

Islam, M.M., Rahaman, A. & Islam, M.R. Development of Smart Healthcare Monitoring System in IoT Environment. Sn Comput. Sci. 1, 185 (2020). https://doi.org/10.1007/s42979-020-00195-y (Year: 2020).*

International Search Report and Written Opinion of PCT/US2021/033441 dated Sep. 16, 2021, 13 pages.

Extended European Search Report of European Patent Application Serial No. EP21808241.0, May 23, 2024, 9 pages.

* cited by examiner

GATEWAY DEVICE FACILITATING COLLECTION AND MANAGEMENT OF DATA FROM A BODY AREA NETWORK TO A STUDY COORDINATING SYSTEM

TECHNICAL FIELD

The present disclosure relates to the field of physiology, wireless communication, and data management.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Scientific study often requires a large sample size in order to get an accurate assessment of a population. One problem that arises with physiological studies is that fitting each patient or other subject with the correct measurement sensors, and then recording data from those sensors, is logistically difficult and time consuming.

Another problem is that if the sensors are wired then all of the subjects must stay connected to the measuring equipment during the study, which makes it difficult to study physiological data during activities such as sports, running, workouts, or even the physical events of a normal work day.

Yet another problem is that registering each patient or subject and synchronizing each measurement system with the study can be a time-consuming process. This may discourage some people from participating in the study, which can skew the results of the study because the participants are not entirely random.

SUMMARY

One illustrative, non-limiting objective of this disclosure is to provide systems, devices, methods, and kits for quick and convenient addition of patients or other subjects to be added to a study, and for such patients and other subjects to have their biometric or other physiologic metric data collected in real time and outside of a clinical setting.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In some embodiments, a gateway device comprises at least one processing device comprising a processor coupled to a memory, at least one network interface, and at least one sensor device interconnect. The at least one processing device is configured to pair one or more sensor devices of a body area network associated with a subject with the gateway device utilizing the at least one sensor device interconnect. Pairing the one or more sensor devices comprises identifying sensing capabilities of the one or more sensor devices. The at least one processing device is also configured to provide, to a study coordinating system over a first network connection established utilizing the at least one network interface, a gateway identifier for the gateway device and information characterizing the identified sensing capabilities of the one or more sensor devices paired with the gateway device. The at least one processing device is further configured to receive, from the study coordinating system over the first network connection, one or more study parameters for at least one study to be conducted involving the subject, the one or more study parameters identifying data to be collected from at least one of the one or more sensor devices paired with the gateway device. The at least one processing device is further configured to collect the identified data from the at least one sensor device paired with the gateway device over a second network connection established utilizing the at least one network interface, and to provide the collected data to the study coordinating system over the first network connection.

The first network connection may comprise a long-range wireless network connection and the second network connection may comprise a short-range wireless network connection. The short-range network connection may utilize an ultra-low power wireless communication protocol.

The at least one sensor device interconnect may comprise a physical mount for attaching a given sensor device to the gateway device. The physical mount may comprise a magnetic interconnect for attaching the given sensor device to the gateway device.

The at least one sensor device interconnect may also or alternatively comprise one or more inductive coils configured to charge a given one of the one or more sensor devices when the given sensor device is in close physical proximity to the at least one sensor device interconnect.

The at least one sensor device interconnect may comprise one or more photodetectors and transmitters configured for high-speed data transfer with a given one of the one or more sensor devices when aligned with corresponding photodetectors and transmitters of the given sensor device.

In some embodiments, the at least one sensor device interconnect comprises one or more signal generators. The one or more signal generators may be configured to generate an electric field in a vicinity of the at least one sensor device interconnect. Pairing a given one of the one or more sensor devices with the gateway device may comprise receiving a signal from the given sensor device characterizing the generated electric field, and parsing the received signal to confirm placement and identification of the given sensor device relative to the at least one sensor device interconnect. Pairing a given one of the one or more sensor devices with the gateway device may also or alternatively comprise identifying configuration parameters for the given sensor device and generating a configuration signal comprising the identified configuration parameters for delivery to the given sensor device utilizing the one or more signal generators. The identified configuration parameters may comprise at least one of one or more programming data commands, one or more configuration commands, one or more unique identifiers, and one or more sensor calibration signals.

The gateway identifier for the gateway device may comprise at least one of a bar code, a quick response code, and a radio frequency identifier.

The gateway device may further comprise a data storage component. The at least one processing device may be further configured to buffer the collected data in the data storage component prior to providing the collected data to the study coordinating system over the first network connection. Buffering the collected data in the data storage component may be performed responsive to detecting disruption of the first network connection. Detecting disruption of the first network connection may comprise determining that the first network connection is at least one of unavailable, intermittent, and experiencing reduced available bandwidth.

The at least one processing device may be further configured to apply at least one of compression and encryption to the collected data prior to providing the collected data to the study coordinating system over the first network connection.

The one or more study parameters received from the study coordinating system may further identify stimulus to be applied to the subject as part of the at least one study. The at least one processing device may be further configured to provide one or more commands to initiate application of stimulus to the subject over the second network connection to at least one stimulating device paired with the gateway device. The at least one stimulating device may comprise or be the same as at least one of the one or more sensor devices.

In some embodiments, a computer program product comprises a non-transitory processor-readable storage medium having stored therein executable program code which, when executed, causes at least one processing device of a gateway device to pair one or more sensor devices of a body area network associated with a subject with the gateway device utilizing at least one sensor device interconnect of the gateway device. Pairing the one or more sensor devices comprise identifying sensing capabilities of the one or more sensor devices. The executable program code when executed also causes the at least one processing device to provide, to a study coordinating system over a first network connection established utilizing at least one network interface of the gateway device, a gateway identifier for the gateway device and information characterizing the identified sensing capabilities of the one or more sensor devices paired with the gateway device. The executable program code when executed further causes the at least one processing device to receive, from the study coordinating system over the first network connection, one or more study parameters for at least one study to be conducted involving the subject. The one or more study parameters identify data to be collected from at least one of the one or more sensor devices paired with the gateway device. The executable program code when executed further causes the at least one processing device to collect the identified data from the at least one sensor device paired with the gateway device over a second network connection established utilizing the at least one network interface, and to provide the collected data to the study coordinating system over the first network connection.

In some embodiments, a method comprises pairing one or more sensor devices of a body area network associated with a subject with a gateway device utilizing at least one sensor device interconnect of the gateway device. Pairing the one or more sensor devices comprises identifying sensing capabilities of the one or more sensor devices. The method also comprises providing, to a study coordinating system over a first network connection established utilizing at least one network interface of the gateway device, a gateway identifier for the gateway device and information characterizing the identified sensing capabilities of the one or more sensor devices paired with the gateway device. The method further comprises receiving, from the study coordinating system over the first network connection, one or more study parameters for at least one study to be conducted involving the subject. The one or more study parameters identify data to be collected from at least one of the one or more sensor devices paired with the gateway device. The method further comprises collecting the identified data from the at least one sensor device paired with the gateway device over a second network connection established utilizing the at least one network interface, and providing the collected data to the study coordinating system over the first network connection. The method is performed by at least one processing device comprising a processor coupled to a memory.

BRIEF DESCRIPTION OF THE DRAWINGS

Several aspects of the disclosure can be better understood with reference to the following drawings. In the drawings, like reference numerals designate corresponding parts throughout the several views.

DETAILED DESCRIPTION

Figure 1:
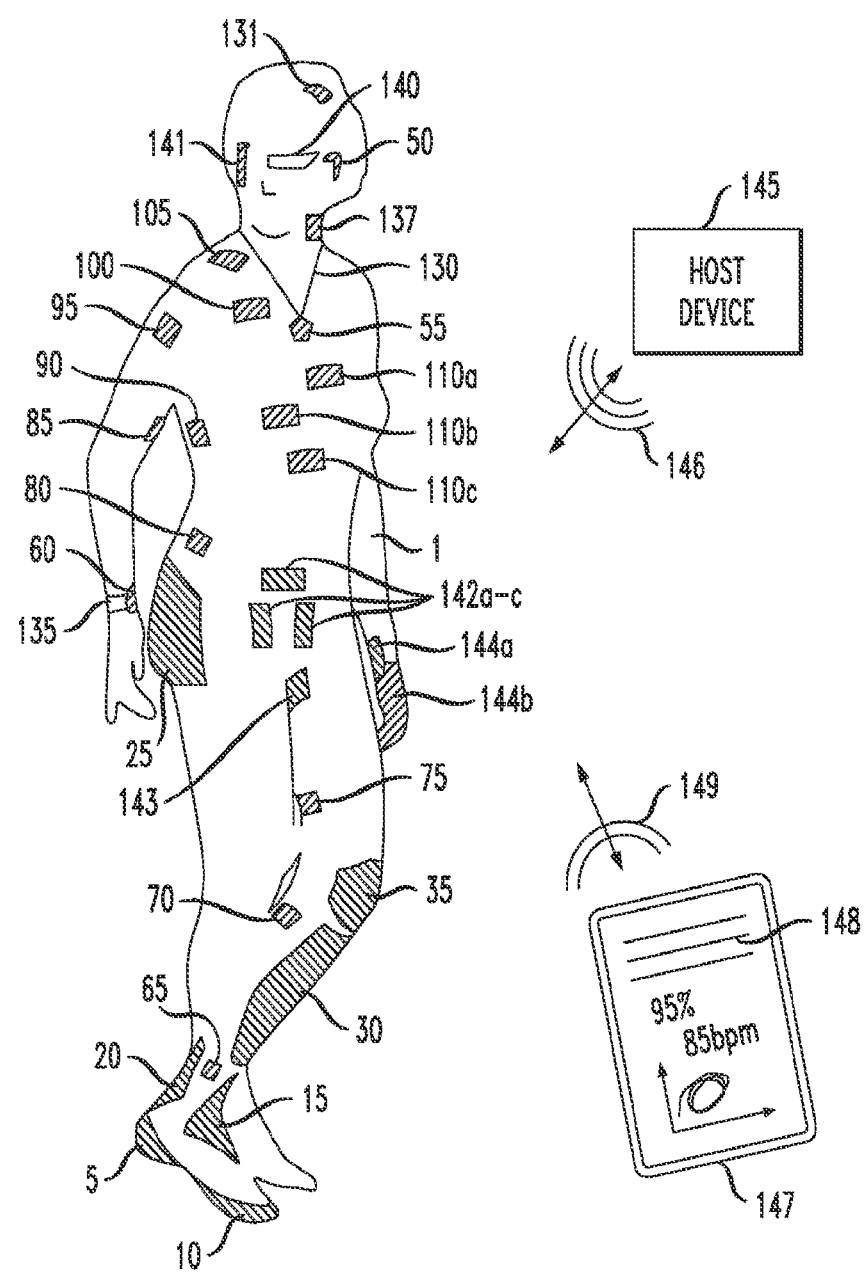
FIG. 1 illustrates aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The accompanying drawings illustrate various embodiments of systems, methods, and embodiments of various other aspects of the disclosure. One of ordinary skill in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. It is also noted that components and elements in the figures are not necessarily drawn to scale, emphasis instead being placed upon illustrating principles.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

One illustrative, non-limiting objective of this disclosure is to provide systems, devices, methods, and kits for monitoring physiologic and/or physical signals from a subject. Another illustrative, non-limiting objective is to provide simplified systems for monitoring subjects. Another illustrative, non-limiting objective is to provide comfortable long-term wearable systems for monitoring subjects. Yet another illustrative, non-limiting objective is to provide systems for facilitating interaction between a user and a subject with regard to physiologic monitoring of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

A modular physiologic monitoring system in accordance with the present disclosure is configured to monitor one or more physiologic and/or physical signals, also referred to herein as physiologic parameters, of a subject (e.g., a human subject, a patient, an athlete, a trainer, an animal such as equine, canine, porcine, bovine, etc.). The modular physiologic monitoring system may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may also include one or more modules, configured and dimensioned to mate with corresponding ones of the one or more patches, and to interface with the subject therethrough. In aspects, one or more module interconnects included within the one or more modules may be sized and dimensioned to interface with one or more corresponding interconnects included within the patch interface, wherein to form an operable interconnection between a given patch interface and a given module, the given patch interface may first be coupled to the subject (e.g., so as to maintain the shape thereof during the process of coupling the given patch interface to the given module). One or more of the modules may be configured to convey and/or store one or more physiologic and/or physical signals, signals derived therefrom, and/or metrics derived therefrom obtained via the interface with the subject.

Each module may include a power source (e.g., a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (e.g., physiologic and/or physical signals), stimulus, etc.

One or more of the patches may include one or more interconnects, configured and dimensioned so as to couple with one or more of the modules, said modules including a complementary interconnect configured and dimensioned to couple with the corresponding patch. The patch may include a bioadhesive interface for attachment to the subject, the module retainable against the subject via interconnection with the patch.

In aspects, the patch may be configured so as to be single use (e.g., disposable). The patch may include a thin, breathable, stretchable laminate. In aspects, the laminate may include a substrate, a bioadhesive, one or more sensing or stimulating elements in accordance with the present disclosure, and one or more interconnects for coupling one or more of the sensing elements with a corresponding module.

In aspects, to retain a high degree of comfort and long term wearability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the now freestanding patch is sufficiently frail such that the patch can no longer substantially retain the predetermined shape (e.g., sufficiently frail such that the patch will not survive in a free standing state). In aspects, stretch applied to the patch while removing the patch from the subject may result in snap back once the patch is in a freestanding state that renders such a patch to crumple into a ball and no longer function. Removal of the patch interface from the skin of the subject may result in a permanent loss in shape of the patch interface without tearing of the patch interface. In aspects, the interconnect may be sufficiently frail such that removal of the patch interface from the skin of the subject may result in a permanent loss of shape of the interconnect.

In aspects, the patch may include a film (e.g., a substrate), with sufficiently high tear strength, such that, as the patch is peeled from the skin of a subject, the patch does not tear. In aspects, the ratio between the tear strength of the patch and the peel adhesion strength of the patch to skin (e.g., tear strength:peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 Newtons per millimeter (N/mm), greater than 0.1 N/mm, greater than 0.25 N/mm, greater than 0.50 N/mm, greater than 0.75 N/mm, greater than 2 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers. In aspects, a patch interface in accordance with the present disclosure may have a ratio between the tear strength of the patch and the peel tack of the adhesive to mammalian skin is greater than 8:1, greater than 4:1, greater than 2:1, or the like.

In aspects, the patch may be provided with a characteristic thickness of less than 50 micrometers (µm), less than 25 µm, less than 12 µm, less than 8 µm, less than 4 µm, or the like. Yet, in aspects, a balance between the thickness, stiffness, and tear strength may be obtained so as to maintain sufficiently high comfort levels for a subject, minimizing skin stresses during use (e.g., minimizing skin stretch related discomfort and extraneous signals as the body moves locally around the patch during use), minimizing impact on skin health, minimizing risk of rucking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 grams per meter squared per 24 hours (g/m$^2$/24 hrs) and 20,000 g/m$^2$/24 hrs, between 500 g/m$^2$/24 hrs and 12,000 g/m$^2$/24 hrs, between 2,000 g/m$^2$/24 hrs and 8,000 g/m$^2$/24 hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complementary electrically conducting connectors, configured and dimensioned so as to mate together upon attachment. In the case of an inductively or capacitively coupled interconnect, the patch and module may include complementary coils or electrodes configured and dimensioned so as to mate together upon attachment.

Each patch or patch-module pair may be configured as a sensing device to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like. Each patch and/or patch-module pair may also or alternatively be configured as a stimulating device to apply a stimulus to the subject in response to signaling from the host device, the signaling being based on analysis of the physiologic and/or physical parameters of the subject measured by the sensing device(s).

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like. In aspects, the host device may include features for recharging and/or performing diagnostic tests on one or more of the modules.

In aspects, the system may include a plurality of modules and associated patch interfaces for placement onto a signal subject, the host device, and/or one or more of the modules configured to coordinate synchronous monitoring of the signals amongst the modules on the subject. In aspects, a host device in accordance with the present disclosure may be integrated into a bedside alarm clock, housed in an accessory, within a purse, a backpack, a wallet, is or is included in a mobile computing device, a smartphone, a tablet computer, a pager, a laptop, a local router, a data recorder, a network hub, a server, a secondary mobile computing device, a repeater, a combination thereof, or the like.

In aspects, a system in accordance with the present disclosure may include a plurality of substantially similar modules (e.g., generally interchangeable modules, but with unique identifiers), for coupling with a plurality of patches, each patch, optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more other patches on the subject, a hub, etc. The data collection from each module may be coordinated through one or more modules and/or with a host device in accordance with the present disclosure. The modules may report a timestamp along with the data in order to synchronize data collection across multiple patch-module pairs on the subject, between subjects, etc. Thus, if a module is to be replaced, a hot swappable replacement (e.g., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use. In aspects, the system may include a plurality of modules, the modules being hot swappable with the patch interface, so as to maintain a nearly continuous or continuous operation thereof.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

In addition to physiologic monitoring, one or more patches and/or modules may be used to provide a stimulus to the subject, as will be described in further detail below.

According to aspects, there is provided use of a modular physiologic monitoring system in accordance with the present disclosure to monitor a subject, to monitor an electrocardiogram (EKG) of a subject, to perform one or more tasks in accordance with the present disclosure, etc.

According to aspects, there is provided an interface (e.g., a patch in accordance with the present disclosure) for monitoring a physiologic, physical, and/or electrophysiological signal from a subject. The interface or patch may include a substrate, an adhesive coupled to the substrate formulated for attachment to the skin of a subject, and one or more sensors and/or electrodes each in accordance with the present disclosure coupled to the substrate, arranged, configured, and dimensioned to interface with the subject. The patch interface may also include one or more interconnects embedded into the substrate for attachment or coupling of the patch to one or more microcircuits (e.g., which may be part of one or more modules), to one or more sensors and/or electrodes attached to or embedded onto the surface of the substrate, etc. The substrate may be formed from an elastic or polymeric material, such that the patch is configured to maintain operation when stretched to more than 25%, more than 50%, or more than 80%. The elastic or polymeric material may include a soft pseudo-elastic material.

According to aspects, there is provided an isolating patch for providing a barrier between a handheld monitoring device with a plurality of contact pads and a subject, including a flexible substrate with two surfaces, a patient facing surface and an opposing surface, and an electrically and/or ionically conducting adhesive coupled to at least a portion of the patient facing surface configured so as to electrically and mechanically couple with the subject when placed thereupon, wherein the conducting adhesive is exposed within one or more regions of the opposing surface of the substrate, the regions patterned so as to substantially match the dimensions and layout of the contact pads. In aspects, the conducting adhesive may include an anisotropically conducting adhesive, with the direction of conduction oriented substantially normal to the surfaces of the substrate.

In aspects, the adhesive may be patterned onto the substrate so as to form one or more exposed regions of the substrate, one or more of the sensors and/or electrodes arranged within the exposed regions. One or more of the electrodes may include an inherently or ionically conducting gel adhesive.

In aspects, one or more of the electrodes may include an electrode feature arranged so as to improve the electrical connection between the electrode and the skin upon placement on a subject. In aspects, the improved electrical connection may be achieved after pressure is applied to the electrode (e.g., after the patch is secured to the subject and then a pressure is applied to the electrode). The electrode feature may include one or more microfibers, barbs, microneedles, or spikes to penetrate into a stratum corneum of the skin. The electrode feature may be configured to penetrate less than 2 mm into the skin, less than 1 mm, less than 0.5 mm, less than 0.2 mm, or the like during engagement therewith. In aspects, a gel adhesive in accordance with the present disclosure located adjacent to the electrode features (e.g., between the features and the skin) may be configured to maintain the improved electrical connection to the skin for more than 1 hour, more than 1 day, or more than 3 days after the electrode contacts the skin or pressure is applied to the electrode.

In aspects, a patch interface in accordance with the present disclosure may include one or more stretchable electrically conducting traces attached to the substrate, arranged so as to couple one or more of the sensors and/or electrodes with one or more of the interconnects.

In aspects, the interconnect may include a plurality of connectors, the connectors physically connected to each other through the substrate. The patch may include an isolating region arranged so as to isolate one or more of the connectors from the skin while the patch is engaged therewith According to aspects, there is provided a device (e.g., a module in accordance with the present disclosure) for monitoring a physiologic, physical, and/or electrophysiological signal from a subject. The module may include a housing, a printed circuit board (PCB) including one or more microcircuits, and an interconnect configured for placement of the device onto a subject interface (e.g., a patch in accordance with the present disclosure). The printed circuit board may constitute at least a portion of the housing in some embodiments. The module may include a three-dimensional antenna coupled to the microcircuits (e.g., coupled with a transceiver, transmitter, radio, etc. included within the microcircuits). In aspects, the antenna may be printed onto or embedded into the housing. In aspects, the antenna may be printed on an interior wall of or embedded into the housing, the circuit board providing a ground plane for the antenna. In aspects, the housing may be shaped like a dome and the antenna may be patterned into a spiraling helix centered within the dome.

In aspects, a module in accordance with the present disclosure may include a sensor coupled with one or more of the microcircuits, the sensor configured to interface with the subject upon attachment of the module to the patch interface. The module may include a sensor and/or microelectronics configured to interface with a sensor included on a corresponding patch interface. In aspects, one or more of the sensors may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, a combination thereof, or the like.

In aspects, the module may be hermetically sealed. The module and/or patch interface may include a gasket coupled to the circuit board or the substrate, the gasket formed so as to isolate the region formed by the module interconnect and the patch from a surrounding environment, when the module is coupled with the patch.

In aspects, the module interconnect may include an electrically conducting magnetic element, and the patch interface may include one or more ferromagnetic regions coupled to the substrate, the magnetic elements arranged so as to physically and/or electrically couple the module to the patch interface when the magnetic elements are aligned with the ferromagnetic regions. In aspects, the ferromagnetic regions may be formed from stretchable pseudo elastic material and/or may be printed onto the substrate. In aspects, the module and/or the patch interface may include one or more fiducial markings to visually assist with the alignment of the module to the patch during coupling thereof.

According to aspects, there is provided a kit for monitoring a physiologic, physical, and/or electrophysiological signal from a subject, including one or more patches in accordance with the present disclosure, one or more modules in accordance with the present disclosure, a recharging bay in accordance with the present disclosure, and one or more accessories in accordance with the present disclosure. One or more of the accessories may include an adhesive removing agent configured to facilitate substantially pain free removal of one or more of the patches from a subject.

According to aspects, there is provided a service system for managing the collection of physiologic data from a customer, including a customer data management service, configured to generate and/or store the customer profile referencing customer preferences, data sets, and/or monitoring sessions, an automated product delivery service configured to provide the customer with one or more monitoring products or supplies in accordance with the present disclosure, and a datacenter configured to store, analyze, and/or manage the data obtained from the customer during one or more monitoring sessions.

In aspects, the service system may include a report generating service configured to generate one or more monitoring reports based upon the data obtained during one or more monitoring sessions, a report generating service coupled to the datacenter configured to generate one or more monitoring reports based upon the data obtained during one or more monitoring sessions, and/or a recurrent billing system configured to bill the customer based upon the number or patches consumed, the data stored, and/or the reports generated throughout the course of one or more monitoring sessions.

According to aspects, there is provided a method for monitoring one or more physiologic and/or electrophysiological signals from a subject, including attaching one or more soft breathable and hypoallergenic devices to one or more sites on the subject, obtaining one or more local physiologic and/or electrophysiological signals from each of the devices, and analyzing the signals obtained from each of the devices to generate a metric, diagnostic, report, and/or additional signals therefrom.

In aspects, the method may include hot swapping one or more of the devices without interrupting the step of obtaining, and/or calibrating one or more of the devices while on the subject. In aspects, the step of calibrating may be performed with an additional medical device (e.g., a blood pressure cuff, a thermometer, a pulse oximeter, a cardiopulmonary assessment system, a clinical grade EKG diagnostic system, etc.).

In aspects, the method may include determining the position and/or orientation of one or more of the devices on the subject, and/or determining the position and/or orientation from a photograph, a video, or a surveillance video.

In aspects, one or more steps of a method in accordance with the present disclosure may be performed at least in part by a device, patch interface, module, and/or system each in accordance with the present disclosure.

According to aspects, there is provided a system for measuring blood pressure of a subject in an ambulatory setting including an EKG device in accordance with the present disclosure (e.g., a patch/module pair in accordance with the present disclosure configured to measure local electrophysiological signals in adjacent tissues), configured for placement onto a torso of the subject, the EKG device configured to measure an electrocardiographic signal from the torso of the subject so as to produce an EKG signal, one or more pulse devices (e.g., patch/module pairs in accordance with the present disclosure configured to measure local blood flow in adjacent tissues) each in accordance with the present disclosure, configured for placement onto one or more sites on one or more extremities of the subject, each of the pulse devices configured to measure a local pulse at the placement site so as to produce one or more pulse signals; and a processor included in or coupled to one or more of the EKG devices and the pulse devices, the processor configured to receive the EKG signal, the pulse signals, and/or signals generated therefrom, the processor including an algorithm, the algorithm configured to analyze one or more temporal metrics from the signals in combination with one or more calibration parameters, to determine the blood pressure of the subject.

In aspects, the system for monitoring blood pressure of a subject may include a blood pressure cuff configured to produce a calibration signal, the processor configured to generate one or more of the calibration parameters, from the calibration signal in combination with the EKG signal, and pulse signals.

In aspects, one or more of the devices may include an orientation sensor, the orientation sensor configured to obtain an orientation signal, the processor configured to receive the orientation signal or a signal generated therefrom, and to incorporate the orientation signal into the analysis. Some non-limiting examples of orientation sensors include one or more of an altimeter, a barometer, a tilt sensor, a gyroscope, combinations thereof, or the like.

A system for measuring the effect of an impact on physiologic state of a subject including an electroencephalogram (EEG) device (e.g., a patch/module pair in accordance with the present disclosure configured to measure local electrophysiological signals associated with brain activity in adjacent tissues) in accordance with the present disclosure, configured for placement behind an ear, on the forehead, near a temple, onto the neck of the subject, or the like, the EEG device configured to measure an electroencephalographic signal from the head of the subject so as to produce an EEG signal, and configured to measure one or more kinetic and/or kinematic signals from the head of the subject so as to produce an impact signal, and a processor included in or coupled to the EEG device, the processor configured to receive the EEG signal, the impact signals, and/or signals generated therefrom, the processor including an algorithm, the algorithm configured to analyze the impact signals to determine if the subject has suffered an impact, to separate the signals into pre impact and post impact portions and to compare the pre and post impact portions of the EEG signal, to determine the effect of the impact on the subject.

In aspects, the EEG device may include additional sensors such as a temperature sensor configured to generate a temperature signal from the subject or a signal generated therefrom, the processor configured to receive the temperature signal and to assess a thermal state of the subject therefrom. In aspects, the EEG device may include a hydration sensor configured to generate a fluid level signal from the subject, the processor configured to receive the fluid level signal or a signal generated therefrom, and to assess the hydration state of the subject therefrom.

In aspects, the EEG device and/or the processor may include or be coupled to a memory element, the memory element including sufficiently large space to store the signals for a period of 3 μminutes, 10 μminutes, 30 μminutes, or 1 hour.

In aspects, the system for measuring the effect of an impact on physiologic state of a subject may include an EKG device (e.g., a patch/module pair in accordance with the present disclosure configured to measure local electrophysiological signals in adjacent tissues) in accordance with the present disclosure, the EKG device configured for placement onto the torso or neck of the subject, the EKG device configured to measure an electrophysiological signal pertaining to cardiac function of the subject so as to produce an EKG signal, the processor configured to receive the EKG signal or a signal generated therefrom, the algorithm configured so as to incorporate the EKG signal into the assessment. In aspects, the processor may be configured to extract a heart rate variability (HRV) signal from the EKG signal, a pre impact and post impact portion of the HRV signal compared to determine at least a portion of the effect of the impact.

According to aspects, there is provided a system for assessing a sleep state of a subject including an electromyography (EMG)/electrooculography (EOG) device (e.g., a patch/module pair in accordance with the present disclosure configured to measure local electromyographic and/or electrooculographic signals from adjacent tissues), in accordance with the present disclosure, configured for placement behind an ear, on a forehead, substantially around an eye, near a temple, or onto a neck of the subject, the EMG/EOG device configured to measure one or more electromyographic and/or electrooculographic signals from the head or neck of the subject so as to produce an EMG/EOG signal, and a processor included in or coupled to the EMG/EOG device, the processor configured to receive the EMG/EOG signal, and/or signals generated therefrom, the processor including an algorithm, the algorithm configured to analyze the EMG/EOG signal, to determine the sleep state of the subject.

In aspects, the EMG/EOG device may include a microphone, the microphone configured to obtain an acoustic signal from the subject, the processor configured to receive the acoustic signal or a signal generated therefrom, the algorithm configured so as to incorporate the acoustic signal into the assessment.

In aspects, the system may include a sensor for evaluating oxygen saturation (SpO2) at one or more sites on the subject to obtain an oxygen saturation signal from the subject, the processor configured to receive the oxygen saturation signal or a signal generated therefrom, the algorithm configured so as to incorporate the oxygen saturation signal into the assessment.

In aspects, the processor may include a signal analysis function, the signal analysis function configured to analyze the EMG/EOG signals, the acoustic signal, and/or the oxygen saturation signal to determine the sleep state of the subject, identify snoring, identify a sleep apnea event, identify a bruxism event, identify a rapid eye movement (REM) sleep state, identify a sleep walking state, a sleep talking state, a nightmare, or identify a waking event. In aspects, the system may include a feedback mechanism, configured to interact with the subject, a user, a doctor, a nurse, a partner, a combination thereof, or the like. The processor may be configured to provide a feedback signal to the feedback mechanism based upon the analysis of the sleep state of the subject. The feedback mechanism may include a transducer, a loudspeaker, tactile actuator, a visual feedback means, a light source, a buzzer, a combination thereof, or the like to interact with the subject, the user, the doctor, the nurse, the partner, or the like.

A modular physiologic monitoring system, in some embodiments, includes one or more sensing devices, which may be placed or attached to one or more sites on the subject. Alternatively or additionally, one or more sensing devices may be placed "off" the subject, such as one or more sensors (e.g., cameras, acoustic sensors, etc.) that are not physically attached to the subject. The sensing devices are utilized to establish whether or not an event is occurring and to determine one or more characteristics of the event by monitoring and measuring physiologic parameters of the subject. The determination of whether an event has occurred or is occurring may be made by a device that is at least partially external and physically distinct from the one or more sensing devices, such as a host device in wired or wireless communication with the sensing devices as described below with respect to FIG. 1. The modular physiologic monitoring system includes one or more stimulating devices, which again may be any combination of devices that are attached to the subject or placed "off" the subject, to apply a stimulus to the subject in response to a detected event. Various types of stimulus may be applied, including but not limited to stimulating via thermal input, vibration input, mechanical input, a compression or the like with an electrical input, etc.

The sensing devices of a modular physiologic monitoring system, such as patch-module pairs described below with respect to FIG. 1, may be used to monitor one or more physiologic functions or parameters of a subject, as will be described in further detail below. The sensing devices of the modular physiologic monitoring system, or a host device configured to receive data or measurements from the sensing devices, may be utilized to monitor for one or more events (e.g., through analysis of signals measured by the sensing devices, from metrics derived from the signals, etc.). The stimulating devices of the modular physiologic monitoring system may be configured to deliver one or more stimuli (e.g., electrical, vibrational, acoustic, visual, etc.) to the subject. The stimulating devices may receive a signal from one or more of the sensing devices or a host device, and provide the stimulation in response to the received signal.

FIG. 1 shows aspects of a modular physiologic monitoring system in accordance with the present disclosure. In FIG. 1, a subject 1 is shown with a number of patches and/or patch-module pairs each in accordance with the present disclosure attached thereto at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. In some embodiments, the feedback devices 135, 140 may also or alternatively function as stimulating devices. The host device 145, the user device 147, the patches and/or patch-module pairs, and/or the feedback devices 135, 140 may be configured for wireless communication 146, 149 during a monitoring session.

In aspects, a patch-module pair may be adapted for placement almost anywhere on the body of a subject 1. As shown in FIG. 1, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring and/or stimulating sites is generally determined based upon the intended application of the patch-module pairs described herein.

Additional placement sites on the abdomen, perineal region 142a-c, genitals, urogenital triangle, anal triangle, sacral region, inner thigh 143, or the like may be advantageous in the assessment of autonomic neural function of a subject. Such placements regions may be advantageous for assessment of parasympathetic nervous system (PNS) activity, somatosensory function, assessment of sympathetic nervous system (SNS) functionality, etc.

Placement sites on the wrist 144a, hand 144b or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygonaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received a procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," PCT application serial no. PCT/US2015/043123, published as WO 2016/019250 and titled "Modular Physiologic Monitoring Systems, Kits, and Methods," and PCT application Ser No. PCT/US2017/030186, published as WO 2017/190049 and titled "Monitoring and Management of Physiologic Parameters of a Subject," the disclosures of which are incorporated by reference herein in their entirety.

In some embodiments, modular physiologic monitoring systems may include sensing and stimulating devices that are physically distinct, such as sensing and stimulating devices that are physically attached to a subject at varying locations. For example, the sensing and stimulating devices may include different ones of the patch-module pairs described above with respect to FIG. 1. In other embodiments, one or more devices may provide both monitoring and stimulating functionality. For example, one or more of the patch-module pairs described above with respect to FIG. 1 may be configured to function as both a sensing device and a stimulating device. It is to be appreciated, however, that embodiments are not limited solely for use with the patch-module pairs of FIG. 1 as sensing and stimulating devices. Various other types of sensing and stimulating devices may be utilized, including but not limited to sensors that are "off-body" with respect to subject 1.

The sensing and/or stimulating devices of a modular physiologic monitoring system may be configured for radio frequency (RF) or other wireless and/or wired connection with one another and/or a host device. Such RF or other connections may be used to transmit or receive feedback parameters or other signaling between the sensing and stimulating devices. The feedback, for example, may be provided based on measurements of physiologic parameters that are obtained using the sensing devices to determine when events related to cardiac output are occurring. Various thresholds for stimulation that are applied by the stimulating devices may, in some embodiments, be determined based on such feedback. Thresholds may relate to the amplitude or frequency of electric or other stimulation. Thresholds may also be related to whether to initiate stimulation by the stimulating devices based on the feedback.

During and/or after stimulus is applied with the stimulating devices, the sensing devices may monitor the physiologic response of the subject. If stimulation is successful in achieving a desired response, the stimulation may be discontinued. Otherwise, the type, timing, etc. of stimulation may be adjusted.

In some embodiments, a user of the modular physiologic monitoring system may set preferences for the stimulus type, level, and/or otherwise personalize the sensation during a setup period or at any point during use of the modular physiologic monitoring system. The user of the modular physiologic monitoring system may be the subject being monitored and stimulated by the sensing devices and stimulating devices, or a doctor, nurse, physical therapist, medical assistant, caregiver, etc. of the subject being monitored and stimulated. The user may also have the option to disconnect or shut down the modular physiologic monitoring system at any time, such as via operation of a switch, pressure sensation, voice operated instruction, etc.

Stimulus or feedback which may be provided via one or more stimulating devices in a modular physiologic monitoring system may be in various forms, including physical stimulus (e.g., electrical, thermal, vibrational, pressure, stroking, a combination thereof, or the like), optical stimulus, acoustic stimulus, etc.

Physical stimulus may be provided in the form of negative feedback, such as in a brief electric shock or impulse as described above. Data or knowledge from waveforms applied in conducted electrical weapons (CEWs), such as in electroshock devices, may be utilized to avoid painful stimulus. Physical stimulus may also be provided in the form of positive feedback, such as in evoking pleasurable sensations by combining non-painful electrical stimulus with pleasant sounds, music, lighting, smells, etc. Physical stimulus is not limited solely to electrical shock or impulses. In other embodiments, physical stimulus may be provided by adjusting temperature or other stimuli, such as in providing a burst of cool or warm air, a burst of mist, vibration, tension, stretch, pressure, etc.

Feedback provided via physical stimulus as well as other stimulus described herein may be synchronized with, initiated by or otherwise coordinated or controlled in conjunction with one or more monitoring devices (e.g., a host device, one or more sensing devices, etc.). The monitoring devices may be connected to the stimulating devices physically (e.g., via one or more wires or other connectors), wirelessly (e.g., via radio or other wireless communication), etc. Physical stimulus may be applied to various regions of a subject, including but not limited to the wrist, soles of the feet, palms of the hands, nipples, forehead, ear, mastoid region, the skin of the subject, etc.

Optical stimulus may be provided via one or more stimulating devices. The optical stimulus may be positive or negative (e.g., by providing pleasant or unpleasant lighting or other visuals). Acoustic stimulus similarly may be provided via one or more stimulating devices, as positive or negative feedback (e.g., by providing pleasant or unpleasant sounds). Acoustic stimulus may take the form of spoken words, music, etc. Acoustic stimulus, in some embodiments may be provided via smart speakers or other electronic devices such as Amazon Echo®, Google Home®, Apple Home Pod®, etc. The stimulus itself may be provided so as to elicit a particular psychophysical or psychoacoustic effect in the subject, such as directing the subject to stop an action, to restart an action (such as breathing), to adjust an action (such as a timing between a step and a respiratory action, between a muscle contraction and a leg position, etc.).

As described above, the modular physiologic monitoring system may operate in a therapeutic mode, in that stimulation is provided when one or more cardiac parameters of a subject indicate some event (e.g., actual, imminent or predicted failure or worsening). The modular physiologic monitoring system, however, may also operate as or provide a type of cardiac "pacemaker" in other embodiments. In such embodiments, the modular physiologic monitoring system has the potential to reduce the frequency of cardiac events, or to possibly avoid certain cardiac events altogether. A modular physiologic monitoring system may provide functionality for timing and synchronizing periodic compression and relaxation of microvascular blood vessel networks with cardiac output. Such techniques may be utilized to respond to a type of failure event as indicated above. Alternatively or additionally, such techniques may be provided substantially continuously, so as to improve overall cardiac performance (e.g., blood flow) with the same or less cardiac work.

In some embodiments, a modular physiologic monitoring system may be configured to provide multi-modal stimuli to a subject. Multi-modal approaches use one or more forms of stimulation (e.g., thermal and electrical, mechanical and electrical, etc.) in order to mimic another stimulus to trick local nerves into responding in the same manner to the mimicked stimulus. In addition, in some embodiments multi-modal stimulus or input may be used to enhance a particular stimulus. For example, adding a mimicked electrical stimulus may enhance the effect of a thermal stimulus.

Modular physiologic monitoring systems may use pulses across space and time (e.g., frequency, pulse trains, relative amplitudes, etc.) to mimic vibration, comfort or discomfort, mild or greater pain, wet sensation, heat/cold, training neuroplasticity, taste (e.g., using a stimulating device placed in the mouth or on the tongue of a subject to mimic sour, sweet, salt, bitter or umami flavor), tension or stretching, sound or acoustics, sharp or dull pressure, light polarization (e.g., linear versus polar, the "Haidinger Brush"), light color or brightness, etc.

Stimulus amplification may also be provided by one or more modular physiologic monitoring systems using multi-modal input. Stimulus amplification represents a hybrid approach, wherein a first type of stimulus may be applied and a second, different type of stimulus provided to enhance the effect of the first type of stimulus. As an example, a first stimulus may be provided via a heating element, where the heating element is augmented by nearby electrodes or other stimulating devices that amplify and augment the heating stimulus using electrical mimicry in a pacing pattern. Electrical stimulus may also be used as a supplement or to mimic various other types of stimulus, including but not limited to vibration, heat, cold, etc. Different, possibly unique, stimulation patterns may be applied to the subject, with the central nervous system and peripheral nervous system interpreting such different or unique stimulation patterns as different stimulus modalities.

Another example of stimulus augmentation is sensing a "real" stimulus, measuring the stimulus, and constructing a proportional response by mimicry such as using electric pulsation. The real stimulus, such as sensing heat or cold from a Peltier device, may be measured by electrical-thermal conversion. This real stimulus may then be amplified using virtual mimicry, which may provide energy savings and the possibility of modifying virtual stimulus to modify the perception of the real stimulus.

In some embodiments, the stimulating devices in a modular physiologic monitoring system include an electrode array that attaches (e.g., via an adhesive or which is otherwise held in place) to a preferred body part. One or more of the stimulating devices may include a multiplicity of both sensing and stimulation electrodes, including different types of sensing and/or stimulation electrodes. The sensing electrodes on the stimulation devices, in some embodiments, may be distinct from the sensing devices in the modular physiologic monitoring system in that the sensing devices in the modular physiologic monitoring system may be used to measure physiologic parameters of the subject while the sensing electrodes on the stimulation devices in the modular physiologic monitoring system may be utilized to monitor the application of a stimulus to the subject.

A test stimulus may be initiated in a pattern in the electrode array, starting from application via one or a few of the stimulation electrodes and increasing in number over time to cover an entire or larger portion of the electrode array. The test stimulus may be used to determine the subject's response to the applied stimulation. Sensing electrodes on the stimulation devices may be used to monitor the application of the stimulus. The electrode array may also be used to record a desired output (e.g., physiologic parameters related to cardiac output). As such, one or more of the electrodes in the array may be configured so as to measure the local evoked response associated with the stimulus itself. Such an approach may be advantageous to confirm capture of the target nerves during use. By monitoring the neural response to the stimulus, the stimulus parameters including amplitude, duration, pulse number, etc. may be adjusted while ensuring that the target nerves are enlisted by the stimulus in use.

The test stimulus may migrate or be applied in a pattern to different electrodes at different locations in the electrode array. The response to the stimulus may be recorded or otherwise measured, using the sensing devices in the modular physiologic monitoring system and/or one or more of the sensing electrodes of the stimulating devices in the modular physiologic monitoring system. The response to the test stimulus may be recorded or analyzed to determine an optimal sensing or application site for the stimulus to achieve a desired effect or response in the subject. Thus, the test stimulus may be utilized to find an optimal sensing (e.g., dermatome driver) location. This allows for powerful localization for optimal pacing or other application of stimulus, which may be individualized for different subjects.

A stimulating device applied to the subject via an adhesive (e.g., an adhesively applied stimulating device), may be in the form of a disposable or reusable unit, such as a patch and/or patch-module or patch/hub pair as described above with respect to FIG. 1. An adhesively applied stimulating device, in some embodiments, includes a disposable interface configured so as to be thin, stretchable, able to conform to the skin of the subject, and sufficiently soft for comfortable wear. The disposable interface may be built from very thin, stretchable and/or breathable materials, such that the subject generally does not feel the device on his or her body.

The adhesively applied stimulating device also includes a means for interfacing with the subject through an adhesive interface and/or a window in the adhesive interface. Such means may include a plurality of electrodes that are coupled with a reusable component of the adhesively applied stimulating device and that are coupled to the body of the subject through the adhesive interface. The means may also or alternatively include: a vibrating actuator to provide vibration normal to and/or transverse to the surface of the skin on which the adhesively applied stimulating device is attached to the subject; a thermal device such as a Peltier device, a heating element, a cooling element, an RF heating circuit, an ultrasound source, etc.; a means for stroking the skin such as a shape memory actuator, an electroactive polymer actuator, etc.; a means for applying pressure to the skin such as a pneumatic actuator, a hydraulic actuator, etc.

Actuation means of the adhesively applied stimulating device may be applied over a small region of the applied area of the subject, such that the adhesive interface provides the biasing force necessary to counter the actuation of the actuation means against the skin of the subject.

Adhesively applied stimulating devices may be provided as two components—a disposable body interface and a reusable component. The disposable body interface may be applied so as to conform to the desired anatomy of the subject, and wrap around the body such that the reusable component may interface with the disposable component in a region that is open and free from a natural interface between the subject and another surface.

An adhesively applied stimulating device may also be a single component, rather than a two component or other multi-component arrangement. Such a device implemented as a single component may include an adhesive interface to the subject including two or more electrodes that are applied to the subject. Adhesively applied stimulating devices embodied as a single component provide potential advantages such as easier application to the body of the subject, but may come at a disadvantage with regards to one or more of breathability, conformity, access to challenging interfaces, etc. relative to two component or multi-component arrangements.

A non-contacting stimulating device may be, for example an audio and/or visual system, a heating or cooling system, etc. Smart speakers and smart televisions or other displays are examples of audio and/or visual non-contacting stimulation devices. A smart speaker, for example, may be used to provide audible stimulus to the subject in the form of an alert, a suggestion, a command, music, other sounds, etc. Other examples of non-contacting stimulating devices include means for controlling temperature such as fans, air conditioners, heaters, etc.

One or more stimulating devices may also be incorporated in other systems, such as stimulating devices integrated into a bed, chair, operating table, exercise equipment, etc. that a subject interfaces with. A bed, for example, may include one or more pneumatic actuators, vibration actuators, shakers, or the like to provide a stimulus to the subject in response to a command, feedback signal or control signal generated based on measurement of one or more physiologic parameters of the subject utilizing one or more sensing devices.

Although the disclosure has discussed devices attached to the body for monitoring aspects of the subject's disorder and/or physiologic information, as well as providing a stimulus, therapeutic stimulus, etc. alternative devices may be considered. Non-contacting devices may be used to obtain movement information, audible information, skin blood flow changes (e.g., such as by monitoring subtle skin tone changes which correlate with heart rate), respiration (e.g., audible sounds and movement related to respiration), and the like. Such non-contacting devices may be used in place of or to supplement an on-body system for the monitoring of certain conditions, for applying stimulus, etc. Information captured by non-contacting devices may, on its own or in combination with information gathered from sensing devices on the body, be used to direct the application of stimulus to the subject, via one or more stimulating devices on the body and/or via one or more non-contacting stimulating devices.

In some embodiments, aspects of monitoring the subject utilizing sensing devices in the modular physiologic monitoring system may utilize sensing devices that are affixed to or embodied within one or more contact surfaces, such as surfaces on a piece of furniture on which a subject is positioned (e.g., the surface of a bed, a recliner, a car seat, etc.). The surface may be equipped with one or more sensors to monitor the movement, respiration, HR, etc. of the subject. To achieve reliable recordings, it is advantageous to have such surfaces be well positioned against the subject. It is also advantageous to build such surfaces to take into account comfort level of the subject to keep the subject from feeling the sensing surfaces and to maintain use of the sensing surface over time.

Stimulating devices, as discussed above, may take the form of audio, visual or audiovisual systems or devices in the sleep space of the subject. Examples of such stimulating devices include smart speakers. Such stimulating devices provide a means for instruction a subject to alter the sleep state thereof. The input or stimulus may take the form of a message, suggestion, command, audible alert, musical input, change in musical input, a visual alert, one or more lights, a combination of light and sound, etc. Examples of such non-contacting stimulating devices include systems such as Amazon Echo®, Google Home®, Apple Home Pod®, and the like.

Figure 2A:
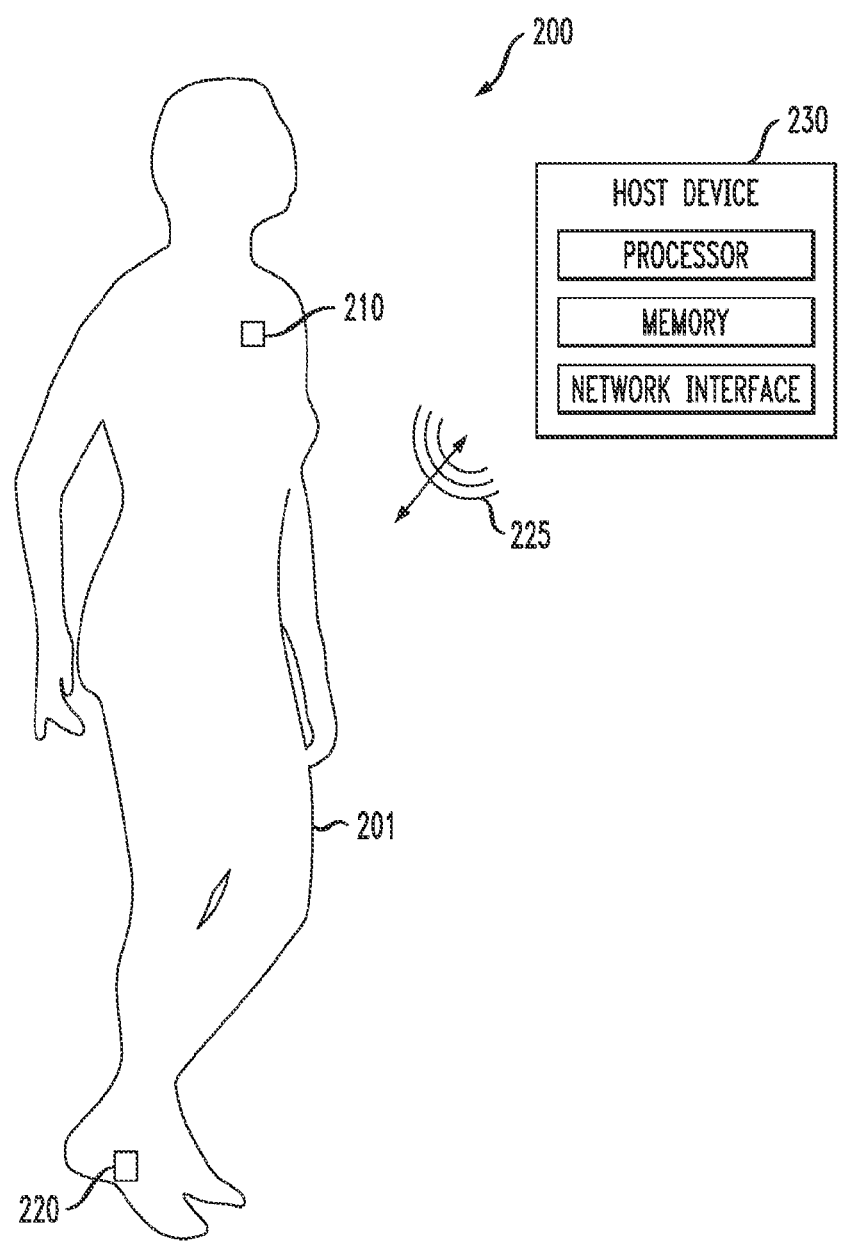
FIGS. 2A-2C illustrate a modular physiologic monitoring system, according to an embodiment of the invention.
Figure 2B:
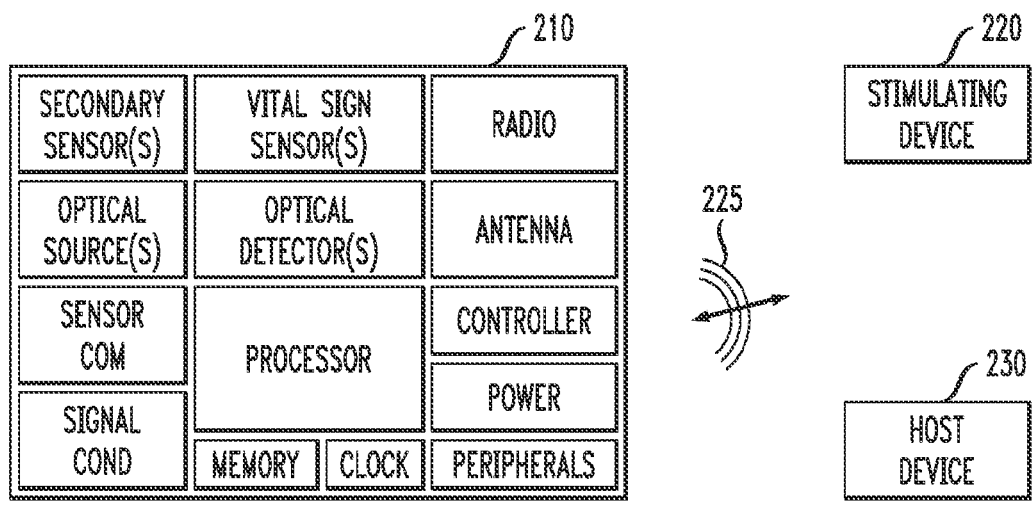
Figure 2C:
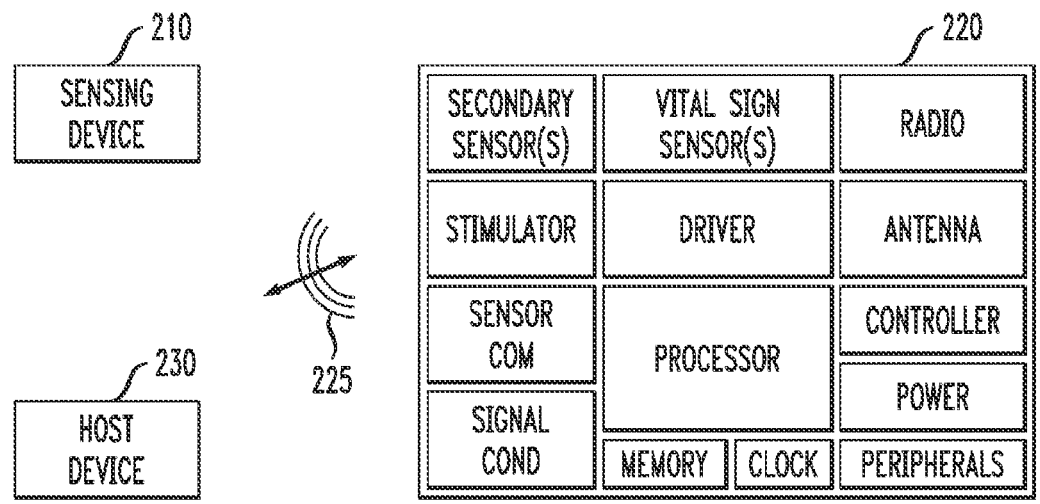

FIGS. 2A-2C show a modular physiologic monitoring system 200. The modular physiologic monitoring system 200 includes a sensing device 210 and a stimulating device 220 attached to a subject 201 that are in wireless communication 225 with a host device 230. The host device 230 includes a processor, a memory and a network interface.

The processor may comprise a microprocessor, a microcontroller, an application-specific integrated circuit (ASIC), a field-programmable gate array (FPGA) or other type of processing circuitry, as well as portions or combinations of such circuitry elements.

The memory may comprise random access memory (RAM), read-only memory (ROM) or other types of memory, in any combination. The memory and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor may load the computer program code from the memory and execute the code to provide the functionalities of the host device 230.

The network interface provides circuitry enabling wireless communication between the host device 230, the sensing device 210 and the stimulating device 220.

FIG. 2A illustrates a modular physiologic monitoring system 200 that includes only a single instance of the sensing device 210 and the stimulating device 220 for clarity. It is to be appreciated, however, that modular physiologic monitoring system 200 may include multiple sensing devices and/or multiple stimulating devices. In addition, although FIG. 2A illustrates a modular physiologic monitoring system 200 in which the sensing device 210 and the stimulating device 220 are attached to the subject 201, embodiments are not limited to such arrangements. As described above, one or more sensing and/or stimulating devices may be part of contacting surfaces or non-contacting devices. In addition, the placement of sensing device 210 and stimulating device 220 on the subject 201 may vary as described above. Also, the host device 230 may be worn by the subject 201, such as being incorporated into a smartwatch or other wearable computing device. The functionality provided by host device 230 may also be provided, in some embodiments, by one or more of the sensing device 210 and the stimulating device 220. In some embodiments, as will be described in further detail below, the functionality of the host device 230 may be provided at least in part using cloud computing resources.

FIG. 2B shows a schematic diagram of aspects of the sensing device 210 in modular physiologic monitoring system 200. The sensing device 210 includes one or more of a processor, a memory device, a controller, a power supply, a power management and/or energy harvesting circuit, one or more peripherals, a clock, an antenna, a radio, a signal conditioning circuit, optical source(s), optical detector(s), a sensor communication circuit, vital sign sensor(s), and secondary sensor(s). The sensing device 210 is configured for wireless communication 225 with the stimulating device 220 and host device 230.

FIG. 2C shows a schematic diagram of aspects of the stimulating device 220 in modular physiologic monitoring system 200. The stimulating device 220 includes one or more of a processor, a memory device, a controller, a power supply, a power management and/or energy harvesting circuit, one or more peripherals, a clock, an antenna, a radio, a signal conditioning circuit, a driver, a stimulator, vital sign sensor(s), a sensor communication circuit, and secondary sensor(s). The stimulating device 220 is configured for wireless communication 225 with the sensing device 210 and host device 230.

Communication of data from the sensing devices and/or stimulating devices (e.g., patches and/or patch-module pairs) may be performed via a local personal communication device (PCD). Such communication in some embodiments takes place in two parts: (1) local communication between a patch and/or patch-module pair (e.g., via a hub or module of a patch-module pair) and the PCD; and (2) remote communication from the PCD to a back-end server, which may be part of a cloud computing platform and implemented using one or more virtual machines (VMs) and/or software containers. The PCD and back-end server may collectively provide functionality of the host device as described elsewhere herein.

Figure 3:
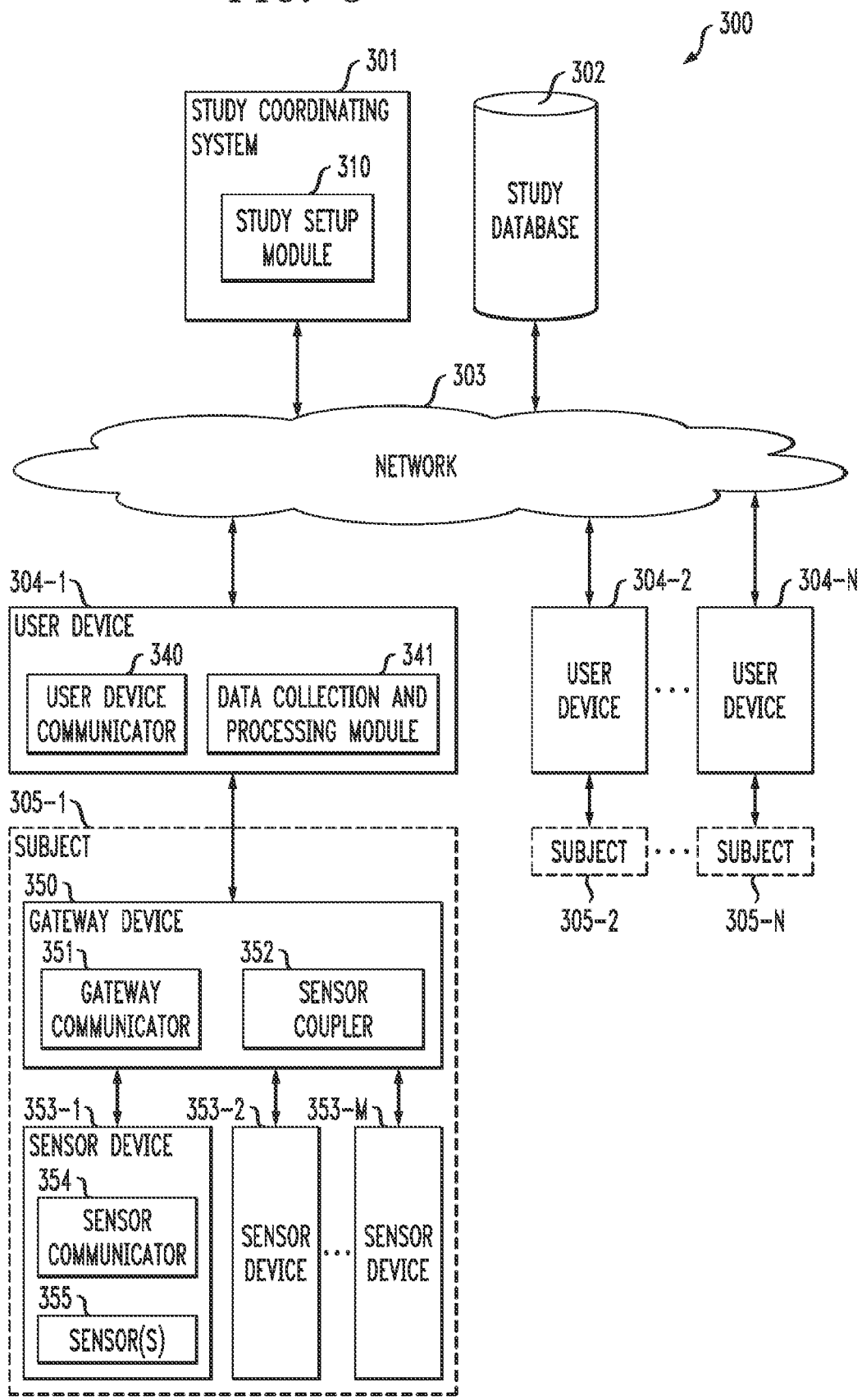
FIG. 3 illustrates a study coordinating system with capability for simple body network to long-range gateway data collection with rapid onboarding and data management, according to an embodiment of the invention.

Illustrative embodiments provide systems and techniques for communication from a body area network (BAN) to a long-range network connection using a gateway device, the gateway device providing functionality for rapid onboarding of devices in the BAN, and for managing data collected from the devices in the BAN. FIG. 3 shows a system 300 configured with such functionality. The system 300 includes a study coordinating system 301 and a study database 302 coupled to a network 303. Also coupled to the network 303 is a set of user devices 304-1, 304-2, ... 304-N (collectively, user devices 304) that are in communication with a set of subjects 305-1, 305-2, ... 305-N (collectively, subjects 305).

The network 303 may comprise a physical connection (wired or wireless), the Internet, a cloud communication network, etc. Examples of wireless communication networks that may be utilized include networks that utilize Visible Light Communication (VLC), Worldwide Interoperability for Microwave Access (WiMAX), Long Term Evolution (LTE), Wireless Local Area Network (WLAN), ultra-wide band (UWB), Infrared (IR) communication, Public Switched Telephone Network (PSTN), radio waves, and other communication techniques.

The study coordinating system 301, in some embodiments, is implemented as an application or applications running on one or more physical or virtual computing resources. Physical computing resources include, but are not limited to, a smartphone, laptop, tablet, desktop, wearable computing device, server, etc. Virtual computing resources include, but are not limited to, VMs, software containers, etc. The physical and/or virtual computing resources implementing the study coordinating system 301, in some embodiments, may be part of a cloud computing platform. A cloud computing platform includes one or more clouds providing a scalable network of computing resources (e.g., including one or more servers and databases). In some embodiments, the clouds of the cloud computing platform implementing the study coordinating system 301 are accessible via the Internet. In other embodiments, the clouds of the cloud computing platform implementing the study coordinating system 301 may be private clouds where access is restricted (e.g., such as to one or more credentialed medical professionals or other authorized users). In these and other embodiments, the study coordinating system 301 may be considered as forming part of an emergency health network comprising at least one server and at least one database (e.g., the study database 302) storing data pertaining to one or more patients (e.g., one or more of the subjects 305) that are part of one or more studies, to settings for one or more studies, etc.

The study database 302 provides a database configured for storing information about patient conditions for the patients or other users (e.g., subjects 305) that participate in one or more studies managed by the study coordinating system 301. For example, the study database 302 may store information collected from the subjects 305 as described in further detail below. The study database 302 may also store settings for one or more studies. As shown in FIG. 3, the study database 302 is located on or accessible via network 303 and is implemented external to the study coordinating system 301. In other embodiments, however, the study database 302 may be implemented at least in part internal to the study coordinating system 301. The study database 302, for example, may be implemented as part of the same cloud computing platform that implements the study coordinating system 301. The study database 302 may also be located at least in part within a memory or persistent storage of one or more of the user devices 304, gateway devices and/or sensor devices associated with one or more of the subjects 305, etc.

In the FIG. 3 example, the study coordinating system 301 connects with and collects information from the subjects 305 via the user devices 304, which are connected to the network 303. The user devices 304 in turn connect with and collect information from the subjects 305 via respective gateway devices (e.g., user device 304-1 connects with gateway device 350 associated with subject 305-1). In other embodiments, however, the study coordinating system 301 may connect with and collect information directly from the subjects 305 (e.g., without involvement of the user devices 304), such as by communication with the gateway devices associated with the subjects 305 (e.g., where the gateway devices associated with the subjects 305 connect to the network 303).

While FIG. 3 shows an example where there are multiple user devices 304, one for each of the subjects 305, embodiments are not limited to this arrangement. In other embodiments, a single user device 304 may connect with and collect information from multiple ones of the subjects 305. The FIG. 3 example assumes that there is a distinct user device for each of the subjects 305 that is to be included in a study. In other examples, however, a single user device may be used to manage multiple subjects that are to be included in a study (e.g., including where a single user device manages all subjects that are part of a study).

The study coordinating system 301 includes a study setup module 310, which enables a study coordinator to create one or more studies, and to add users (e.g., ones of the subjects 305) to the one or more studies. The study setup module 310 may do so via communication with the user devices 304 over network 303.

The user devices 304 are assumed to be capable of wireless communication, data storage and visual display. The user devices 304, for example, may comprise mobile phones (smartphones), smartwatches, or other types of mobile or other computing devices. User device 304-1 is shown including a user device communicator 340 and a data collection and processing module 341. The user device communicator 340 may comprise one or more network interfaces, including at least one network interface for connecting the user device 304-1 to the network 303 and at least one network interface for connecting the user device 304-1 to gateway device 350 associated with subject 305-1. It should be appreciated that, in some embodiments, a same network interface may be used for connecting to both the network 303 and the gateway device 350. In other embodiments, different network interfaces are used for connecting to the network 303 and the gateway device 350. The data collection and processing module 341 is configured to collect data from the gateway device 350, and optionally apply preprocessing to such data (e.g., deriving physiologic metrics from physiologic signals in the collected data, formatting the collected data for storage in the study database 302, applying compression and/or encryption to the collected data, etc.). Although not shown in FIG. 3 for clarity of illustration, other ones of the user devices 304-2 through 304-N are assumed to be similarly configured with respective user device communicators and data collection and processing modules.

The subject 305-1, as shown in FIG. 3, is associated with gateway device 350. The gateway device 350 includes a gateway communicator 351 and a sensor coupler 352. The gateway device 350 connects with and collects data from one or more sensor devices 353-1, 353-2, . . . 353-M (collectively, sensor devices 353). The collected data is sent from the gateway device 350 to the user device 304-1, which in turn provides the collected data to the study coordinating system 301 and/or study database 302 via network 303. As noted above, in some embodiments the gateway device 350 may be configured for connection to the network 303, such that the collected data from sensor devices 353 may be provided directly from the gateway device 350 to the study coordinating system 301 and/or study database 302 via network 303 bypassing the user device 304-1.

The gateway communicator 351 may provide one or more network interfaces for facilitating communication with the sensor devices 353, the user device 304-1 and/or the network 303. The gateway communicator 351, in some embodiments, may also be configured to communicate with one or more gateway devices other than the gateway device 350. For example, the subject 304-1 may be associated with two or more gateway devices that manage or collect data from two or more different sets of sensor devices. In such embodiments, one of the gateway devices may act as a management gateway device to coordinate data communication from multiple sensor devices and other gateway devices associated with the subject 305-1 to the user device 304-1, the study coordinating system 301, and/or the study database 302. In still other embodiments, the gateway device 350 may be in communication with one or more gateway devices associated with other ones of the subjects 305-2 through 305-N, so as to act as a management gateway device to coordinate data communication from sensor devices associated with multiple ones of the subjects 305. Various other examples are possible.

The gateway device 350 may apply some preprocessing to the collected data from the sensor devices 353 prior to sending the collected data to the user device 304-1, the study coordinating system 301 and/or the study database 302. The gateway communicator 351 may be configured to send and receive data via the Internet or cloud computing platforms. The gateway communicator 351 may comprise one or more network interfaces configured for communication using VLC, WiMAX, LTE, WLAN, UWB, IR communication, radio waves, and other wireless communication techniques.

The sensor coupler 352 of the gateway device 350 is configured to connect with and synchronize the sensor devices 353 to the gateway device 350. This allows the gateway device 350 to identify which of the sensor devices 353 to collect data (e.g., physiologic signals, physiologic metrics derived from the physiologic signals, etc.) from. The sensor coupler 352, in some embodiments, provides for physical docking of one or more of the sensor devices 353 with the gateway device 350. The sensor coupler 352 may also or alternatively be configured for coupling one or more of the sensor devices 353 with the gateway device 350 when they are in close proximity. This close physical proximity, in some embodiments, enables inductive charging of the sensor devices 353. It should be appreciated, however, that synchronization and charging processes need not be grouped together as a single coupling process using the sensor coupler 352 (e.g., distinct processes may be used for synchronizing sensor devices 353 with the gateway device 350, and for charging the sensor devices 353). Although not shown in FIG. 3 for clarity of illustration, other ones of the subjects 305-2 through 305-N are assumed to be associated with gateway devices configured in a manner similar to that of the gateway device 350.

The sensor devices 353 are assumed to be worn on the body of the subject 305-1. In some embodiments, one or more of the sensor devices 353 is embodied as a patch-module pair as described above with respect to FIGS. 1 and 2A-2C. Each of the sensor devices 353 is assumed to comprise at least one sensor. Sensor device 353-1, for example, comprises a sensor communicator 354 and one or more sensors 355. The sensor device 353-1 utilizes the sensor communicator 354 to provide collected data from at least one of the sensors 355 to the gateway device 350, such as via ultra-low power wireless communication. Such ultra-low power wireless communication may include one or more of VLC, WiMAX, LTE, WLAN, UWB, IR communications, radio waves, etc.

In some embodiments, the sensor device 353-1 may include a memory or persistent storage providing a database or other data store for collected data from the sensors 355. This enables the sensor device 353-1 to store collected data for later transmission if there are connection problems between the sensor device 353-1 and the gateway device 350 that prevent real-time communication of data from the sensors 355 to the gateway device 350. In a similar manner, the gateway device 350 may include a memory or persistent storage providing a database or other data store for collected data from the sensor devices 353 enabling the gateway device 350 to store collected data for later transmission if there are connection problems between the gateway device 350 and one or more of the user devices 304, the study coordinating system 301 and the study database 302.

The sensors 355 are configured to detect various physiologic metrics from measured physiological signals of the subject 305-1. In some embodiments, one or more of the sensors 355 is a motion sensor, a humidity sensor, a camera, a microphone, a radiofrequency receiver, a thermal imager, a radar device, a lidar device, an ultrasound device, a speaker, a heart rate sensor, one or more electrodes (e.g., EEG electrodes, EKG electrodes, etc.), combinations thereof, etc. It should be appreciated, however, that various other types of sensors may be used, including any combination of sensor types described herein.

Functioning of the study setup module 310 of the study coordinating system 301 will now be described in further detail with respect to the process flow 400 of FIG. 4. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 4:
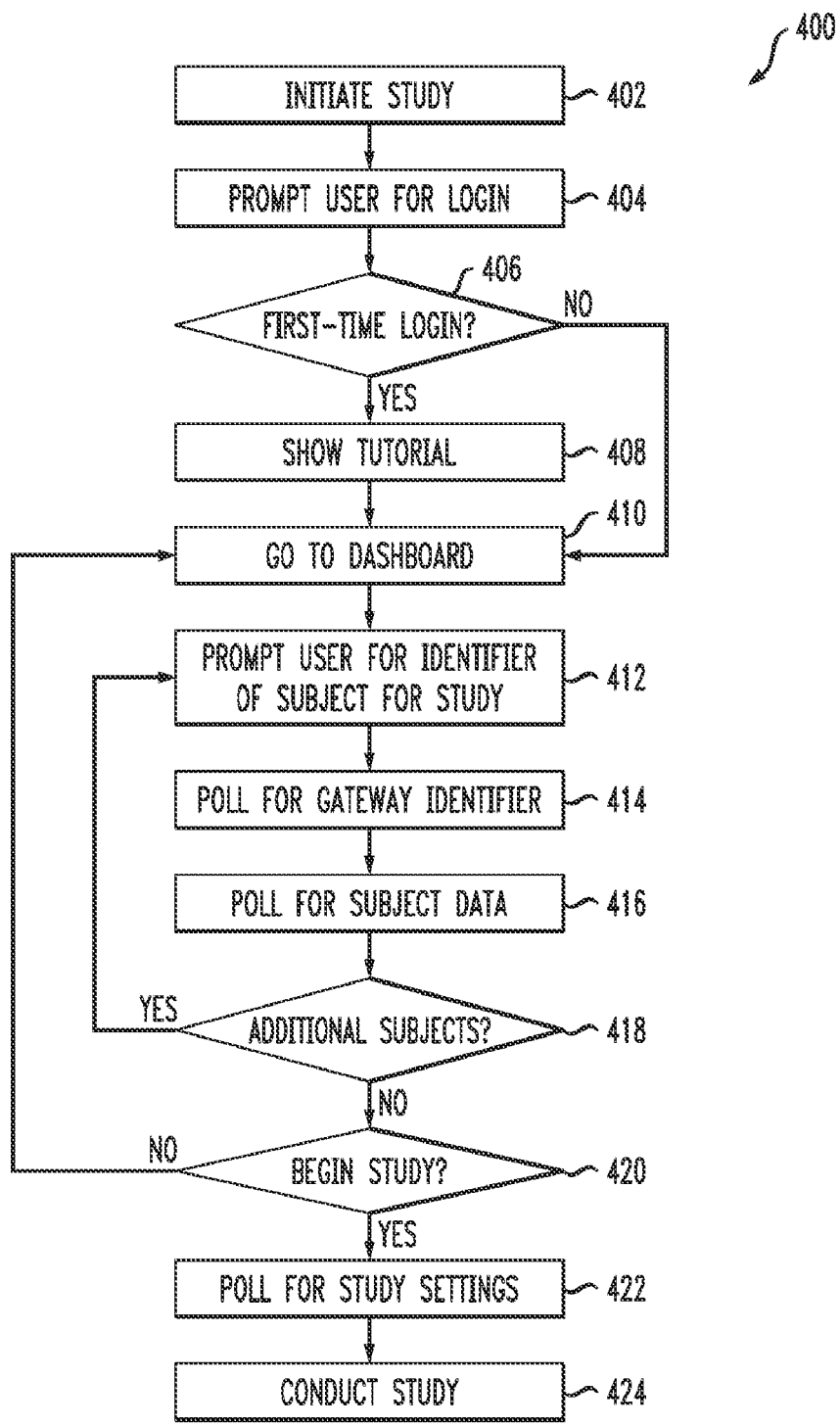
FIG. 4 illustrates a process flow for setting up a physiologic study utilizing a study setup module in the FIG. 3 system, according to an embodiment of the invention.

The process flow 400 of FIG. 4 begins in step 402, initiating a study. Step 402 may be performed by one of the user devices 304 associated with one of the subjects 305. Step 402 may alternatively be performed by another user utilizing another user device or other interface to the study coordinating system 301. It should be appreciated that the user performing step 402 may, but is not required to, be a patient or subject of the study being initiated. In step 404, the user is prompted to login to the study coordinating system 301. Login may be performed using any suitable type of authentication and verification, including the user entering a username and password, providing a key or other proof of identity, using multi-factor authentication, etc. If the user has not previously established login information or an account with the study coordinating system, the user may be prompted to do so as part of step 404.

In step 406, a determination is made as to whether the current user login attempt is a first login attempt for the user. If the result of the step 406 determination is yes, the process flow 400 proceeds to step 408 where an optional tutorial is provided. The tutorial may include a video, a set of written instructions, an interactive or guided tour of a graphical user interface (GUI) dashboard provided by the study coordinating system 301, etc. The tutorial illustratively provides the user with information regarding how to utilize the study coordinating system 301 to set up and conduct studies. The user may be given the option to skip the tutorial if desired. In addition, the tutorial may be accessed in cases where the result of the step 406 determination is no. For example, it may be desired to present the tutorial to users that have not utilized the study coordinating system 301 for longer than some designated threshold period of time, responsive to changes in the GUI dashboard or other functionality provided by the study coordinating system 301, etc. The tutorial may also be accessed from the GUI dashboard of the study coordinating system 301.

If the result of the step 406 determination is no, or following presentation of the tutorial in step 408, the process flow 400 proceeds to step 410 where a dashboard (e.g., a GUI) is presented to the user. The dashboard may include various information related to previous, ongoing, or upcoming studies, options and settings of such studies and/or the study coordinating system 301 itself, current or previously registered patients or subjects, etc. It is assumed, in the FIG. 4 embodiment, that a user selects, from the dashboard (e.g., by activating a user interface feature, such as a button, to "add a patient" or "begin new study"), an option to add one or more patients or subjects to a new or existing study.

The process flow 400 then proceeds to step 412 where the user is prompted for an identifier of a subject (subject ID) that is to be added to the selected study. In the description below, it is assumed that an identifier of subject 305-1 is provided in step 412. In step 414, the study setup module 310 polls for an identifier of a gateway device (gateway device ID) associated with the subject ID received in step 412 (e.g., for an identifier of gateway device 350 associated with subject 305-1). The gateway device ID may comprise a quick response (QR) code, where the QR code may be integrated into or affixed to a housing of the gateway device (such as via a sticker or tag on the gateway device). The QR code may also or alternatively be output on a display of the gateway device. For example, the gateway device may include one or more buttons or other user interface features which cause a display thereof to present the QR code. The gateway device ID may also or alternatively be obtained from a radiofrequency identification (RFID) chip associated with the gateway device, a bar code of the gateway device, via manual entry of a code, etc.

The study setup module 310 in step 416 polls for patient or subject data for the subject being added to the study. In some embodiments, the subject data may be retrieved automatically from a database (e.g., study database 302, from user device 304-1, from gateway device 350) based on the gateway device ID. For example, the subject 305-1 may have biometric or other physiologic data or physiologic metrics stored on one or more of the sensor devices 353, the gateway device 350, the user device 304-1, and the study database 302. The study setup module 310 of the study coordinating system 301 may retrieve such data from any combination of these and other sources utilizing one or both of the subject ID received in step 412 and the gateway device ID received in step 414.

The process flow 400 then proceeds to step 418, where a determination is made as to whether one or more additional subjects are to be added to the study. If the result of the step 418 determination is yes, processing returns to step 412. When the result of the step 418 determination is no, processing proceeds to step 420 where a determination is made as to whether the study should begin. If the result of the step 420 determination is no, processing returns to the dashboard in step 410. From the dashboard, the user may configure settings for the study, initiate, pause or end one or more studies, select to add or remove subjects from one or more studies, review results of one or more studies, monitor progress of one or more ongoing studies, etc. If the result of the step 420 determination is yes, the process flow 400 proceeds to step 422.

In step 422, the study setup module 310 of study coordinating system 301 polls for study settings for the study to be conducted. The study settings may be obtained from the study database 302, from the user initiating the study, combinations thereof, etc. The study settings may include study length, measurement frequency, physiologic metrics to be measured, types of sensing devices and sensors to utilize, etc. Such information may be input by the user, selected from predetermined options, automatically filled in by a pre-loaded study archetype or template, retrieved from the study database 302, combinations thereof, etc. In step 424, the study is conducted in accordance with the selected study settings. Step 424 may include recording or obtaining data from the patients or subjects in the study from respective ones of the user devices 304 associated with the subjects 305 that are part of the study, from gateway devices associated with such subjects 305 that are part of the study, etc. Following step 424, the user may return to the dashboard in step 410.

Figure 5:
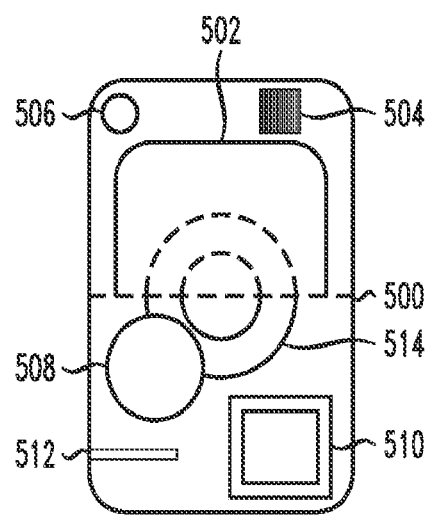
FIG. 5 illustrates a gateway device, according to an embodiment of the invention.
Figure 6:
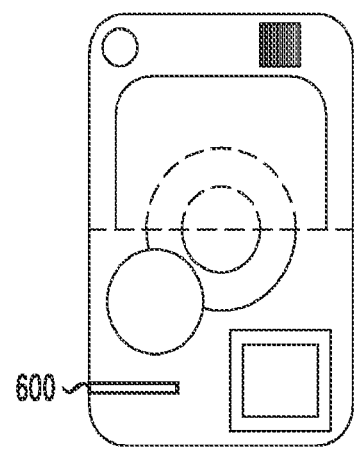
FIG. 6 illustrates a gateway communicator, according to an embodiment of the invention.
Figure 7:
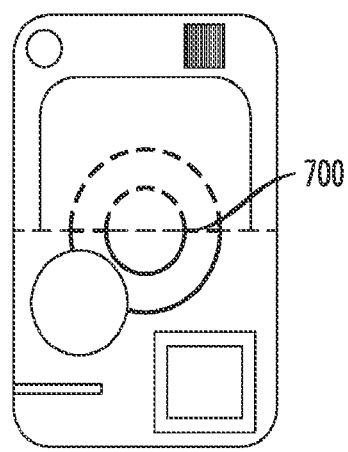
FIG. 7 illustrates a sensor coupler, according to an embodiment of the invention.

Aspects of a gateway device (e.g., gateway device 350) will now be described with respect to FIGS. 5-7. FIG. 5 shows an example of a gateway device 500, which includes an optional mirror 502, gateway device ID or gateway ID 504, hole 506, battery 508, controller 510, gateway communicator 512, and sensor coupler 514. The gateway device 500 may be embodied as a small, transportable and/or wearable device in the form of a key fob, wristband, ring, etc. The gateway device 500 is configured to act as a relay for sensor devices (e.g., sensor devices 353, patch-module pairs as described above with respect to FIGS. 1 and 2A-2C) associated with a subject, such that data from the sensor devices can be sent over a longer distance. Advantageously, this allows the sensor devices to be low-power and therefore smaller than if the sensor devices were required to send information over long distances. The gateway device 500 is shown in FIG. 5 with an optional mirror 502, which facilitates the subject (e.g., 305-1) or an associated caregiver (e.g., a doctor, nurse, physical therapist, study coordinator, etc.) checking that the sensor devices have been placed correctly on parts of the body of the subject that are hard to view directly.

The gateway ID 504 may include a bar code, QR code, RFID, or other information that allows the study coordinating system 301 to quickly associate the gateway device 500 with a particular patient or subject in a study. It should be noted that the gateway ID 504 information may be conveyed from the gateway device 500 to the study coordinating system 301 via one or more other devices, such as one of the user devices 304. The gateway device 500 also includes the hole 506, where a key ring, lanyard, etc. may be attached to the gateway device 500 such that the patient or subject is less likely to lose or misplace the gateway device 500.

The battery 508 of the gateway device 500 is configured to power elements of the gateway device 500 that require electric power. The battery 508 of the gateway device 500 may also be used to charge sensor devices (e.g., sensor devices 353) through inductive charging (e.g., such as when one or more of the sensor devices is mounted or otherwise coupled to sensor coupler 514.

The controller 510 may comprise a computing or processing element or device (e.g., including a processor such as a CPU coupled to a memory) configured to provide various functionality including but not limited to applying processing to data obtained from sensor device before relaying such data to one or more other devices (e.g., user devices 304, the study coordinating system 301, the study database 302, etc.). In some embodiments, such processing includes applying at least one of encryption and compression to the data for easier and more secure transmission.

The gateway communicator 512 is configured to receive data from the sensor devices and provide such data (possibly after processing using controller 510) to one or more other devices (e.g., user devices 304, the study coordinating system 301, the study database 302, etc.). The gateway communicator 512 may also receive data from such other devices regarding the study to be conducted, the type of data to be collected from different sensor devices, the frequency at which data should be collected from different sensor devices, etc.

The sensor coupler 514 is configured to synchronize sensor devices to the gateway device 500, allowing the gateway device 500 to identify which sensor devices are available to receive data from. Such information may be provided to the study coordinating system 301 in some embodiments, so as to allow a user to design a study which takes advantage of the data that is available for measurement using the sensor devices synchronized with the gateway device 500. The sensor coupling process may include physical docking of sensor devices with the gateway device 500, or placing sensor devices and the gateway device 500 in close proximity such that inductive charging can occur. It should be noted, however, that synchronization and charging of sensor devices may be distinct processes.

Functioning of a gateway communicator (e.g., the gateway communicator 512 of gateway device 500, the gateway communicator 351 of gateway device 350) will now be described with respect to FIG. 6. FIG. 6 shows a gateway communicator 600 of a gateway device. The gateway communicator 600 is configured to send and receive data to and from various devices. In some embodiments, the gateway communicator 600 is configured to exchange data over one or more long-range wireless network connections (e.g., the Internet) with user devices 304, study coordinating system 301, study database 302, etc. It should be noted that such exchange of data may include exchange of data with one or more cloud computing platforms implementing such other devices (e.g., a public cloud, private cloud, or hybrid cloud implementing the study coordinating system 301 and/or study database 302). The gateway communicator 600 is also illustratively configured to exchange data over one or more short-range wireless network connections with sensor devices (e.g., sensor devices 353). Such short- and long-range wireless network connections may utilize various communication techniques including but not limited to VLC, WiMAX, LTE, WLAN, UWB, IR communication, radio waves, etc. It should be noted that, in some embodiments, the gateway communicator 600 may provide a physical port for a wired interconnection (e.g., a universal serial bus (USB) interconnection) with one or more other devices (e.g., sensor devices 353, user devices 304, etc.).

Functioning of a sensor coupler (e.g., the sensor coupler 514 of gateway device 500, the sensor coupler 352 of gateway device 350) will now be described with reference to FIG. 7. FIG. 7 shows a sensor coupler 700, which is configured to synchronize sensor devices (e.g., sensor devices 353) to the gateway device, so as to identify which sensor devices the gateway device is able to receive data from. The coupling process may involve physical docking of one or more sensor devices with the gateway device, or placing sensor devices and the gateway device in close proximity such that inductive charging can occur. Again, it should be noted that synchronization and charging processes need not be grouped together and may be distinct processes.

Figure 8:
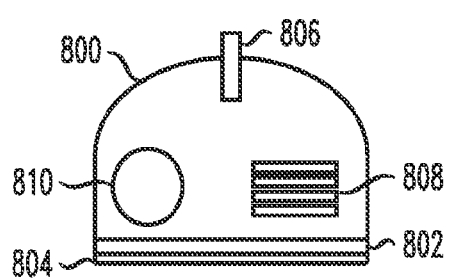
FIG. 8 illustrates a sensor device, according to an embodiment of the invention.
Figure 9:
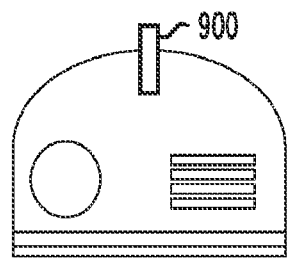
FIG. 9 illustrates a sensor communicator, according to an embodiment of the invention.
Figure 10:
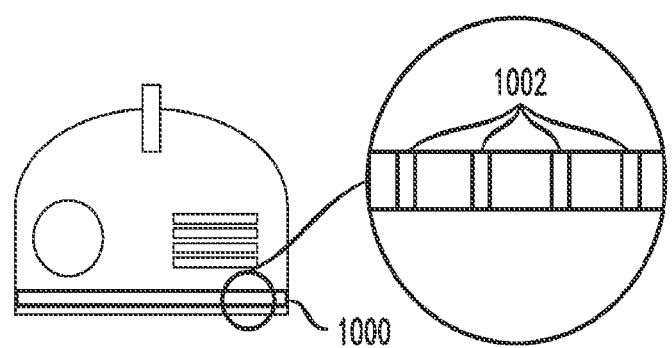
FIG. 10 illustrates a sensor, according to an embodiment of the invention.

Aspects of a sensor device (e.g., sensor devices 353) will now be described with respect to FIGS. 8-10. FIG. 8 shows a sensor device 800 which includes one or more sensors 802, an adhesive surface 804, a sensor communicator 806, a data storage component 808, and a battery 810. The sensors 802 may include one or multiple sensors, including arrangements in which multiple smaller sensors or electrodes collectively provide one larger sensor. The sensors 802 are configured to contact with or be in close proximity to a patient or subject's body such that biometric or physiologic measurement data can be obtained. The adhesive surface 804 is configured to adhere to the patient or subject's skin. The adhesive surface 804 may be reusable or easily replaceable, such that the sensor device 800 may be repositioned as desired on the patient or subject, may be used with different subjects, etc.

The sensor communicator 806 is configured to send data (e.g., measured biometric or physiologic signals, physiologic metrics derived therefrom, etc.) collected by the sensors 802 to a gateway device (e.g., gateway device 500, gateway device 350). The sensor communicator 806 illustratively utilizes ultra-low power wireless communication. The data storage component 808 (e.g., a volatile or non-volatile memory, a persistent storage element) is configured to temporarily store data from the sensors 802 prior to communicating such data to the gateway device in real time. The data storage component 808 may also be utilized for temporary storage of the data from sensors 802 in the event that there are problems communicating with the gateway device such that the data from sensors 802 cannot be provided in real time. The battery 810 is configured to provide power to components of the sensor device 800 that require electrical power.

Functioning of a sensor communicator (e.g., the sensor communicator 806 of sensor device 800, the sensor communicator 354 of sensor device 353-1) will now be described with respect to FIG. 9. FIG. 9 shows a sensor communicator 900, which is configured to exchange data with a gateway device. The sensor communicator 900 is illustratively configured for ultra-low power wireless communication, which may include communication techniques such as VLC, WiMAX, LTE, WLAN, UWB, IR communication, radio waves, etc. The sensor communicator 900 may be completely contained within a housing of a sensor device. The sensor communicator 900 may alternatively comprise a protruding antenna, light or other communication facilitator that extends at least partially outside a housing of a sensor device.

Functioning of a sensor (e.g., the sensors 802 of sensor device 800, the sensors 355 of sensor device 353-1) will now be described with respect to FIG. 10. FIG. 10 shows one or more sensors 1000, which are configured to detect various physiologic or physical metrics of an associated subject. The sensors 1000 may include one or more of motion sensors, temperature sensors, humidity sensors, cameras, microphones, radiofrequency receivers, thermal imagers, radar devices, lidar devices, ultrasound devices, speakers, EEG electrodes, EKG electrodes, heart rate sensors, etc. In some embodiments, the sensors 1000 include an array of small sensors (e.g., including embodiments where an array of small sensors collectively provide one larger sensor). FIG. 10 shows a detailed view of an array of small sensors 1002 providing one larger sensor. Each of the small sensors 1002 in the array may be the same type of sensor, or may be different sensors configured to record different metrics.

In illustrative embodiments, a system includes: one or more wearable sensor devices (e.g., sensor devices 353, sensor device 800) including one or more sensors (e.g., sensors 355 of sensor device 353-1, sensors 802 of sensor device 800, sensors 1000 including an array of small sensors 1002) configured to detect health data of a subject (e.g., one or more health parameters, physiologic signals or physiologic metrics derived therefrom, etc.); a portable gateway device (e.g., gateway device 350, gateway device 500) of a user configured to pair with the wearable sensor devices to enable exchange of health data from the sensors; and at least one computing device (e.g., user devices 304, study coordinating system 301 and study database, etc.) configured to pair with the gateway device to allow exchange of the health data with the gateway device, where the health data includes information detected, measured or otherwise collected using the sensors of the sensor devices. The gateway device is illustratively paired with the at least one computing device such that the health data collected from the sensors of the sensor devices is relayed through the gateway device to the at least one computing device to facilitate conducting one or more health studies.

The sensor devices worn by a subject are assumed to be configured for short-range wireless communication using an ultra-low power communication protocol so as to minimize power consumption by the sensor devices. This, in turn, enables smaller-sized sensor devices to be utilized, increasing comfort and wearability for subjects of a study. It can be challenging to onboard such devices for use in a study, particularly where there are several sensor devices within communication distance of one another. Gateway devices described herein advantageously facilitate rapid onboarding of sensor devices for utilization in one or more studies.

Wireless sensor devices on a subject may be configured for short-range communication only. This helps to save power, reduce a physical size of the sensor devices, and manage network capacity (e.g., as locally transmitted data is seen by fewer overall devices in a crowded space). Illustrative embodiments utilize gateway devices (e.g., a body area to long-range data storage and communication device) which include a plurality of radios, or at least one radio that supports multi-protocol operation. The plurality of radios, or the at least one radio that supports multi-protocol operation, is configured (i) to manage an ultra-low power wireless BAN that includes sensor devices and (ii) to manage a long-range wireless network that includes one or more user devices, a study coordinating system, etc. The gateway device may include a memory or persistent data storage component to store data in case one or both of the wireless connections are intermittent, overwhelmed by traffic, etc. The gateway device may further include a wired connection for transfer of data to other devices.

In some embodiments, a gateway device comprises a hermetically sealed case or housing, within which the radios (e.g., gateway communicator 351 of gateway device 350, gateway communicator 512 of gateway device 500, gateway communicator 600), memory or other data storage component, and power source (e.g., battery 508 of gateway device 500) are contained. The case of the gateway device may be hardened against mechanically harsh and wet environments. The case of the gateway device may further comprise a keyhole (e.g., hole 506 of gateway device 500) where the gateway device can be mounted to a belt, a backpack, a necklace, or the like. The gateway device is illustratively sufficiently small and lightweight so as to be comfortably carried by a subject long-term. For example, the gateway device may be sized so as to fit comfortably within a pocket of a piece of clothing of a user, or in a backpack, a purse, a wallet, clipped to a belt, a weapon, a boot, a helmet, a shoulder clip, etc., so as to be easily carried without notice.

Gateway devices described herein may be further used to support management of a wireless BAN including one or more ultra-low power sensor devices configured to communicate with the gateway device during operation thereof. A gateway device, in some embodiments, may be further configured to manage individual ones or groups of sensors within the ultra-low power sensor devices.

In some embodiments, a gateway device comprises one or more magnetic mounting features or other sensor couplers (e.g., sensor coupler 352, sensor coupler 514), whereby one or more sensor devices may be magnetically mountable to the mounting features of the gateway device. This can facilitate identification and pairing or other synchronization of sensor devices with the gateway device for onboarding to one or more studies. The gateway device may also include an antenna or other feature configured to provide power to one or more of the sensor devices (e.g., through inductive charging) when the sensor devices are mounted on the mounting features and/or are in close physical proximity thereto.

In some embodiments, a gateway device may be provided in a plug over plug configuration wherein the gateway device includes one or more sockets and one or more plugs, such that the gateway device can be plugged into a wall socket without taking up an available socket. Once installed, the gateway device provides all of the functionality described herein while being powered from the wall power. The gateway device may include one or more wireless transport layers, including an ultra-wide band layer, so as to communicate data with associated sensor devices. Such wireless transport layers may also be used by the gateway device to communicate the data into a building network (e.g., a hospital network, a network for a hospital ward, a care ward network, a prison network, a sports arena network, a hotel network, etc.). In such embodiments, the gateway device allows for rapid deployment (e.g., into a hospital or other care facility) without requiring extensive infrastructure reworking.

In some embodiments, the gateway device includes micro-location capability, where the micro-location capability may be enabled using an ultra-wide-band radio and wireless transport layer. The micro-location capability provided by given gateway device advantageously enables effective mapping of sensors and potentially other gateway devices that are in the vicinity of the given gateway device against each other. Such information may be valuable in various use cases, including but not limited to micro-location mapping of users in a network, mapping environmental and sound field effects in the vicinity of users in the network, etc. Such information may also be valuable when combined with data collected from one or more sensors, including for identifying the locations of individuals in need of support, triage, resupply, etc.

In some embodiments, gateway devices configured with micro-location capability may include additional sensors including one or more audio sensors, one or more barometers, one or more impact sensors, one or more environmental sensors (e.g., one or more humidity sensors, temperature sensors, ambient light sensors, ultraviolet light sensors, infrared sensors, millimeter wave sensors, radiation sensors, dry bulb temperature sensors, wet bulb temperature sensors, local airflow sensors, barometers, kinematic sensors, accelerometers, gyroscopes, etc.), combinations thereof, etc. Information from such additional sensors may be used to supplement the information collected from associated sensing devices, including for assisting with local environmental assessment, mapping, etc.

In some embodiments, the combination of sensing devices and gateway devices may be used to provide a pseudo-real-time physiologic assessment and mapping solution to manage a population of subjects and users. In some embodiments, such a system may be deployed into a hospital so as to track and manage continuous patient monitoring throughout the hospital, independent of where in the hospital a patient may be at a given time. Such a system may include mapping functionality provided by an infrared, ultrasound, and/or ultra-wide-band radio so as to track patients and users throughout the hospital. Such a system may be useful for a number of tasks, including but not limited to: tracking a patient location at all times (e.g., to provide answers to the question "Where is my patient?"); providing patient data directly to physicians, nurses, security personnel, and staff no matter where the patient is in the hospital; if a patient is having an emergency situation, a fall while mobile, a fall out of a bed, a heart attack, seizure, or similar event, the patient physiologic state, details of the patient physiology, and the patient location may be immediately be made available to users in the system; providing documented continuous monitoring throughout the entire hospital; differentiating cardiac from neurologic etiology in an emergency event; providing silent "CODE GREEN" (e.g., disturbance) events to security and healthcare staff with pin-pointed location of the disturbance, status, and contextual data around the disturbance; detecting and/or alerting patient "escape" from a room, ward, or location; detecting and/or alerting unauthorized entry; asset tracking; patient family member location and/or communication tracking; assessing ambulation, time mobile, and distance travelled for patients recovering from surgery or undergoing physical therapy; providing cardio-respiratory status of all patients; detecting early signs of fever or other conditions; providing critical care coverage in oncology and hematology wards; etc.

In some embodiments, sensor devices and/or gateway devices may include a processor and memory to store subject metrics, biometrics, allergy data, procedural data, or the like, so as to minimize the possibility of an error while interacting with the subject in a hospital, outpatient, or clinical setting. The system may include one or more localization services so as to provide a secondary confirmation of subject identity during an interaction, etc.

The gateway device and the sensor devices, in some embodiments, comprise companion sensors configured to identify when the sensor devices are mounted to the mounting features of the gateway device. Such companion sensors may be integrated within sensor couplers (e.g., sensor coupler 352, sensor coupler 514) on the gateway device. Existing or dedicated ones of the sensors (e.g., sensors 355 of sensor device 353-1, sensors 802 of sensor device 800, sensors 1000 including an array of small sensors 1002) may be used as companion sensors on the sensor device side. The gateway device may comprise one or more signal generators that are part of the sensor couplers thereof, where the signal generators are configured to generate an electric field in the vicinity of the mounting features. A given sensor device mounted to a given mounting feature of the gateway device is configured to receive the generated signal, and to report one or more characteristics of the signal so as to confirm the placement and identification of the given sensor device on the given mounting feature. The signal generators may also be configured to provide one or more data communication functions with mounted sensor devices. Such data communication may include one or more programming data strings or commands, configuration strings or commands, unique identifiers, sensor calibration signals, etc.

Gateway devices may be configured to communicate with one or more personal electronic devices of a user (e.g., user devices 304), so as to provide notifications, updates or other information that is related to the gateway device or sensor devices (e.g., a power level, connection status, data storage conditions, etc.), data collected from sensors of the sensor devices, etc. The gateway device may also be configured to analyze and process data collected from the sensors of the sensor devices, and to generate one or more signals (e.g., compressed signals, encrypted signals, combinations thereof) for wireless communication over the long-range network.

In one non-limiting example, the sensor devices include patch worn sensors (e.g., as described above with respect to FIGS. 1 and 2A-2C) configured for placement onto the skin of a subject, the patch worn sensors configured so as to monitor an EKG from the subject during operation. The gateway device is configured to receive a digitized signal from the sensor devices corresponding to the EKG, to store the complete or compressed digital signal representation of the EKG locally, to analyze the EKG to extract an R-R interval, heart rate of other metric therefrom, and to communicate one or more signals related to the heart rate or other metric over the long-range wireless network.

A gateway device, in one illustrative use case, is configured to collect a series of sensor data from one or more sensors of one or more sensor devices on a subject using the short-range wireless network. The gateway device is configured to store the raw data, or a compressed and/or encrypted form thereof locally, prior to communication in real or near real time over the long-range network (e.g., a long range (LoRa) low-power wide-area network (LPWAN), a cellular network, an LTE network, a 5G network, etc.). The gateway device may also or alternatively be configured to enable retrospective collection of the stored data over a high-speed wireless (e.g., a WiFi network interface) and/or a wired interface (e.g., a USB 3.1 interface).

In some embodiments, a gateway device is configured to simultaneously collect data from a plurality of sensor devices or sensors thereof, and to manage a BAN associated therewith. The gateway device is configured to extract sensor data and to store the collected data (e.g., in a raw or compressed format) locally for retrospective analysis. Optionally, the gateway device may be configured to transmit the collected data in pseudo real time (e.g., in real time or near real time) over the long-range network connection for pseudo real time analysis thereof.

A gateway device may also be configured to convey a therapeutic signal (e.g., an instruction to provide a stimulus to the subject) to one or more of the sensor devices incorporating stimulation functionality, or to one or more dedicated stimulating devices in the BAN so as to wirelessly perform a closed-loop therapy on the subject. The therapy may include use of transducers of stimulating devices, drug delivery devices, etc. In some embodiments, the therapy is directed based on the data collected from the sensor devices, or may be provided as part of a study to test subject response thereto, etc.

Advantageously, gateway devices may be configured to balance power requirements for the sensor devices along with data storage and processing capabilities. Gateway devices are also configured to manage power-effective transmission from the short-range BAN to long-range communication without having to rely on a personal computing or communication device of the subject. Such configurations advantageously allow for seamless monitoring of a subject using ultra-miniature sensors and sensor devices while maintaining a high degree of edge-computing capability and allowing for ruggedized, long-range data communication from the local device to a remote location.

Figure 11:
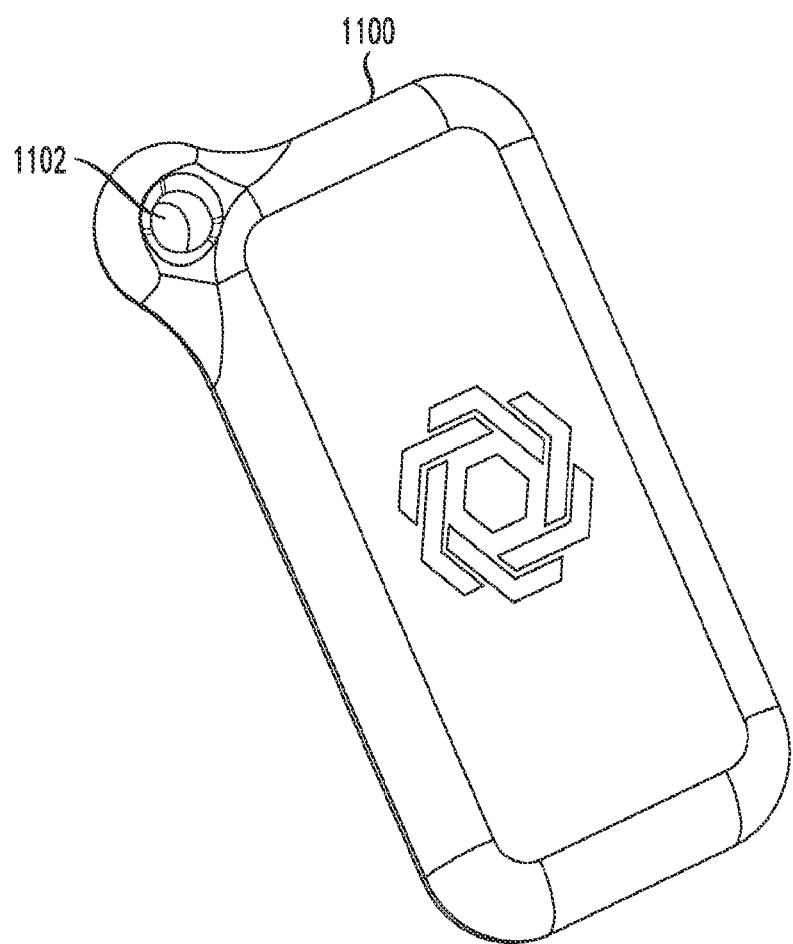
FIG. 11 illustrates a perspective view of a gateway device, according to an embodiment of the invention.

FIG. 11 illustrates a gateway device 1100 embodied as a key fob. The key fob includes a simple means 1102 (e.g., a hole) by which to mount the gateway device 1100 to a keychain, a backpack feature, a belt loop, etc. The gateway device 1100 is hermetically sealed so as to be ruggedized for operation in harsh environments. The gateway device 1100 is assumed to include a plurality of short range and long-range radios sufficient for communicating between one or more BAN sensor devices and one or more long-range remote devices. Although not shown in FIG. 11 for clarity of illustration, it is assumed that the gateway device 1100 includes various internal components such as a power source, a plurality of radios and/or one or more multi-functional radios, a memory, a processor, etc. The gateway device 1100 may also include a wired connector (e.g., a USB connector or port) for offloading data from the onboard memory, for charging the power source of the gateway device 1100. The wired connector may be located at the bottom of the gateway device 1100 for easy slot plugging into a gang-charger or data recovery device.

Figure 12:
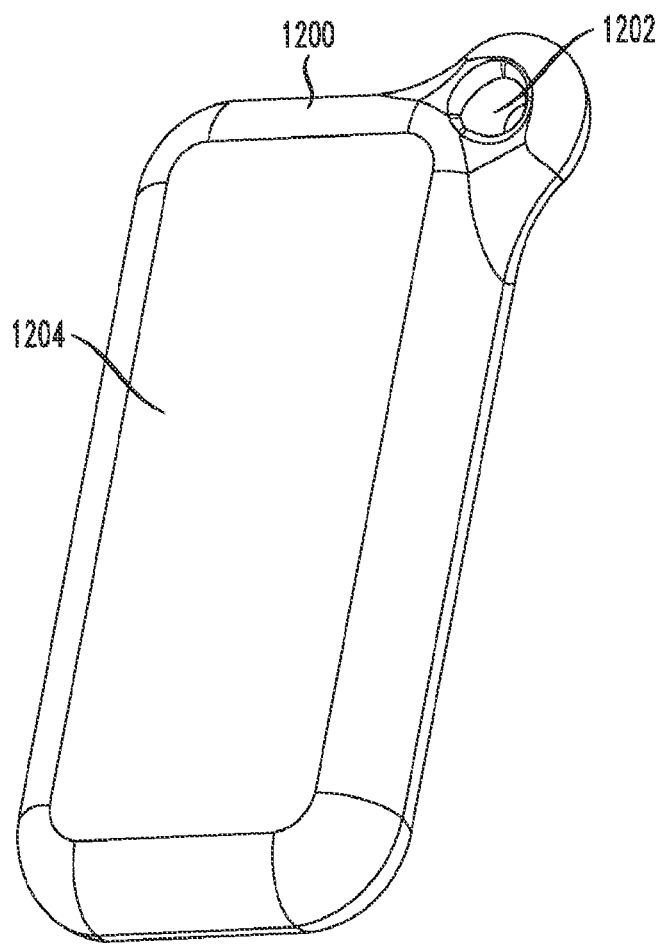
FIG. 12 illustrates a perspective view of a mirror of a gateway device, according to an embodiment of the invention.

FIG. 12 shows a gateway device 1200 including a mounting means 1202 (e.g., a hole) along with a mirror surface 1204 along a face thereof. The mirror surface 1204 enables a user to inspect sensors on their body, and/or to assist in the placement of sensors on their body. The gateway device may include a GPS navigation component, arranged so as to provide long-range location services for the user to which it has been connected.

Figure 13:
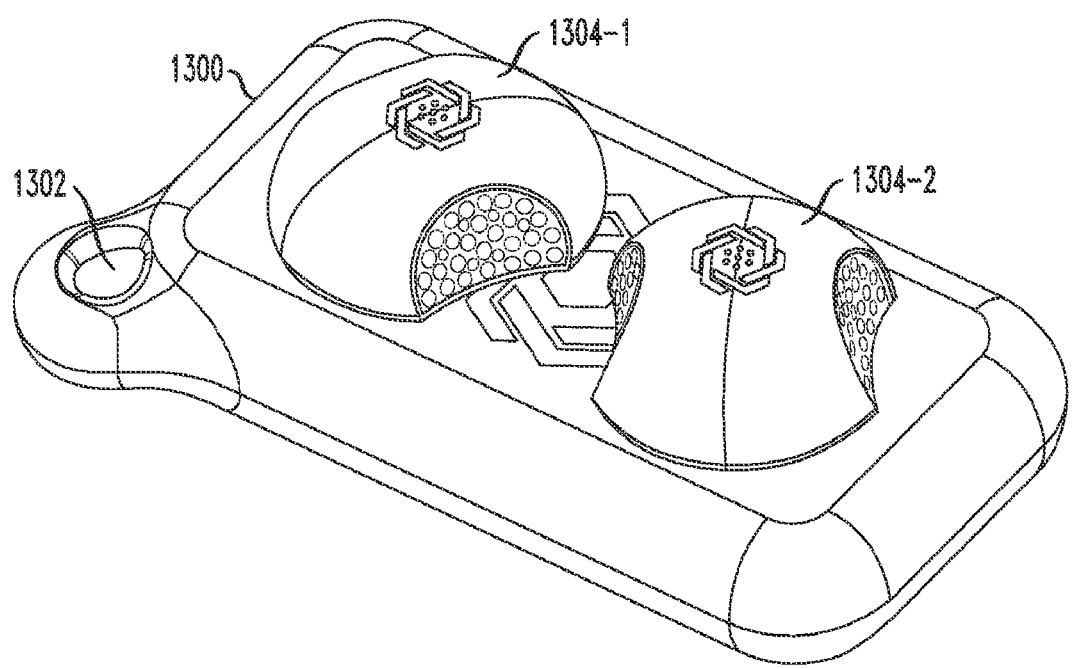
FIG. 13 illustrates a perspective view of a gateway device with two sensor devices mounted thereto, according to an embodiment of the invention.

FIG. 13 shows a gateway device 1300 including a mounting means 1302 (e.g., a hole) along with mounting features (e.g., sensor couplers, which may include integrated signal generators and companion sensors as described above) to which two sensor devices 1304-1 and 1304-2 (collectively, sensor devices 1304) are mated. The gateway device 1300 includes means for privately communicating data with the sensor devices 1304, and/or for wireless charging of the sensor devices 1304 when mounted on the features. The mounting features may be magnetic, such that the sensor devices 1304 are magnetically mounted to the gateway device 1300. The sensor devices 1304 are arranged along features (e.g., which may be defined by the placement of corresponding magnets within the gateway device 1300), so as to be communicatively and/or chargingly coupled with the gateway device 1300. It should be noted that the gateway device 1300 may also include physical features (e.g., recesses) into which the sensor devices 1304 mount.

Advantageously, the entire system can continue to function even when heavily bio-fouled or soiled during use in harsh environments (e.g., as both the gateway device 1300 and the sensor devices 1304 may be hermetically sealed and formed with rugged casings). Further, the gateway device 1300 and sensor devices 1304 may be configured for communication and charging without the need for a physical electrical connection. This is advantageous, as electrical connections can easily become fouled in such environments and thus often represent a failure point for such devices in practice. The gateway device 1300, as noted above, may include small recesses or other physical features in order to facilitate fitting or mounting of the sensor devices 1304 to the gateway device 1300. Such recesses may also provide lateral forces in order to keep the sensor devices 1304 from sliding off the surface of the gateway device 1300 during periods of high activity and movement.

In some embodiments, sensor devices 1304 or sensors included therein may have a low capacitance switch so as to override one or more sensing components on the sensor devices 1304, to as to provide a high-speed signal to communicate with the gateway device 1300 when mounted thereto. Such an arrangement may be advantageous to rapidly offload data stored on the sensor devices 1304 to the gateway device 1300 during a post study download of data. In some embodiments, the sensor devices 1304 and the gateway device 1300 include corresponding photodetectors and transmitters that become aligned when mated together at a mounting feature. The photodetectors and transmitters provide capability for high-speed data transfer there between when mounted together on the feature. The high-speed communication facilitates rapid, ultra-low power exchange of data from the memory of one device to the other privately over the connection created when mounted together.

In some embodiments, the gateway device 1300 may be part of a large collection of gateway devices, each working to monitor one of a plurality of subjects during a study. After completion of the study, the plurality of gateway devices may be collectively connected to one or more data collection/charge stages. The gateway devices may have a conveniently located USB or other physical connector to facilitate rapid and compact wired connection to the data collection/charge stages. The overall system may be advantageous for collecting data during a study with a large number of users or subjects (e.g., during a sporting event, during a marathon, during a concert event, during a museum event, during a training event, during a class, during a pandemic, during a crisis scenario, during an emergency recovery operation, during a first responder scenario, during a mining operation, during use in a hospital setting, etc.). The gateway devices, sensor devices and stages disclosed herein may provide advantageous solutions to optimally manage a study on one or more subjects, providing an optimization of comfort, capability, data capacity, range, and responsiveness that would be challenging to achieve otherwise.

Figure 14:
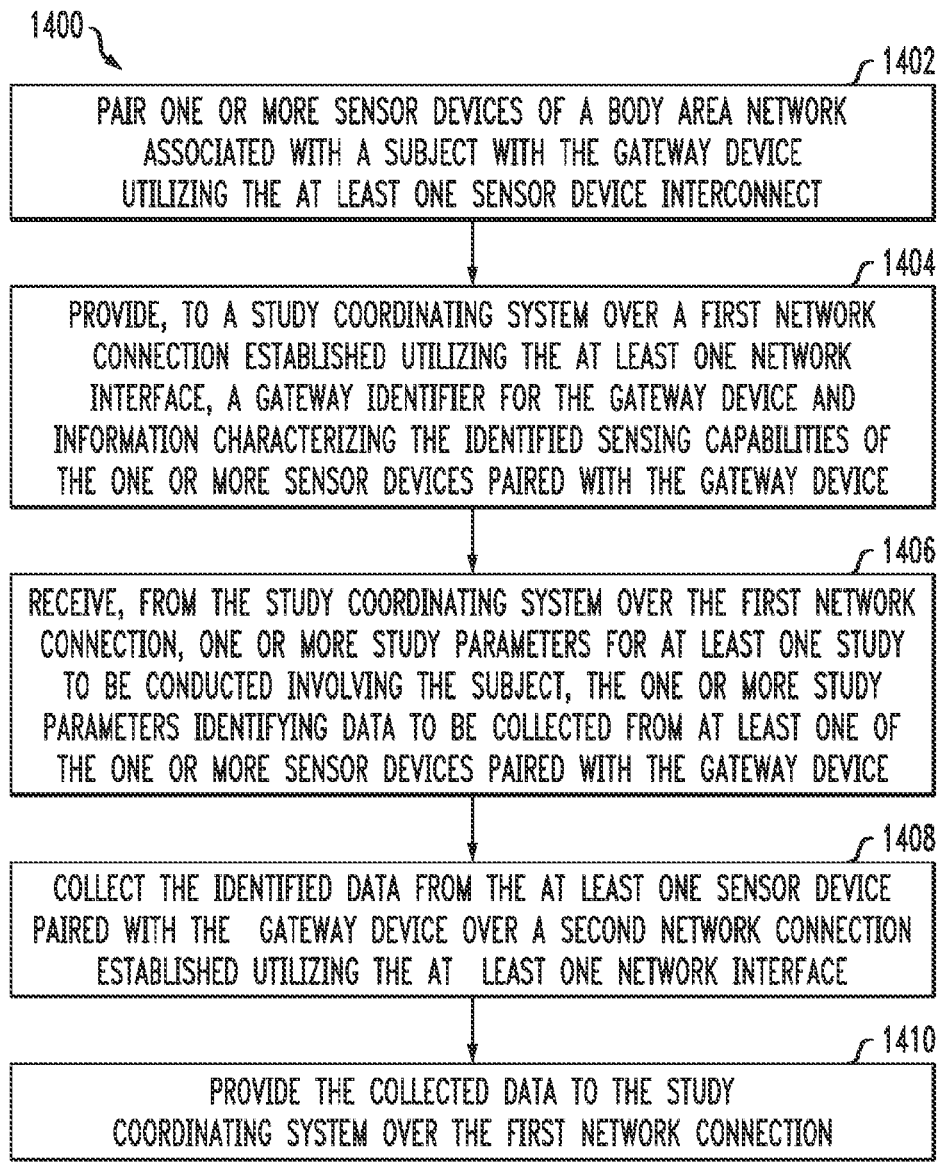
FIG. 14 is a flow diagram of an exemplary process for conducting a study using a gateway device, according to an embodiment of the invention.

An exemplary process 1400 for utilizing a gateway device to conduct a study will now be described with reference to the flow diagram of FIG. 14. It should be understood, however, that this particular process is only an example and that other types of processes for conducting studies utilizing gateway devices may be used in other embodiments as described elsewhere herein. The process 1400 includes steps 1402 through 1410, and is assumed to be performing by a gateway device (e.g., gateway device 350, gateway device 500).

The process 1400 begins with step 1402, pairing one or more sensor devices (e.g., sensor devices 353, sensor device 800) of a BAN associated with a subject (e.g., one or subjects 305) with the gateway device utilizing at least one sensor device interconnect (e.g., sensor coupler 352, sensor coupler 514). Pairing the one or more sensor devices comprises identifying sensing capabilities of the one or more sensor devices.

The at least one sensor device interconnect may comprise a physical mount, such as a magnetic interconnect, for attaching a given sensor device to the gateway device. The at least one sensor device interconnect may also or alternatively comprise one or more inductive coils configured to charge a given one of the one or more sensor devices when the given sensor device is in close physical proximity to the at least one sensor device interconnect. The at least one sensor device interconnect may further or alternatively comprise one or more photodetectors and transmitters configured for high-speed data transfer with a given one of the one or more sensor devices when aligned with corresponding photodetectors and transmitters of the given sensor device.

In some embodiments, the at least one sensor device interconnect comprises one or more signal generators. The one or more signal generators may be configured to generate an electric field in a vicinity of the at least one sensor device interconnect. Pairing a given one of the one or more sensor devices with the gateway device may comprise receiving a signal from the given sensor device characterizing the generated electric field, and parsing the received signal to confirm placement and identification of the given sensor device relative to the at least one sensor device interconnect. Pairing a given one of the one or more sensor devices with the gateway device may also or alternatively comprise identifying configuration parameters for the given sensor device and generating a configuration signal comprising the identified configuration parameters for delivery to the given sensor device utilizing the one or more signal generators. The identified configuration parameters may comprise at least one of one or more programming data commands, one or more configuration commands, one or more unique identifiers, and one or more sensor calibration signals.

In step 1404, a gateway identifier for the gateway device and information characterizing sensing capabilities of the one or more sensor devices paired with the gateway device are provided to a study coordinating system (e.g., study coordinating system 301) over a first network connection established utilizing at least one network interface (e.g., gateway communicator 351, gateway communicator 512) of the gateway device. The gateway identifier or gateway ID may comprise a bar code, a QR code, an RFID, combinations thereof, etc.

One or more study parameters for at least one study to be conducted involving the subject are received in step 1406 from the study coordinating system over the first network connection. The one or more study parameters identify data to be collected from at least one of the one or more sensor devices paired with the gateway device. The one or more study parameters received from the study coordinating system may further identify stimulus to be applied to the subject as part of the at least one study. The process 1400 may further include providing one or more commands to initiate application of stimulus to the subject over the second network connection to at least one stimulating device paired with the gateway device. The at least one stimulating device may comprise or be the same as at least one of the one or more sensor devices.

The identified data is collected in step 1408 from the at least one sensor device paired with the gateway device over a second network connection established utilizing the at least one network interface. In step 1410, the collected data is provided to the study coordinating system over the first network connection. In some embodiments, step 1410 includes applying at least one of compression and encryption to the collected data prior to providing the collected data to the study coordinating system over the first network connection. The first network connection may comprise a long-range wireless network connection and the second network connection may comprise a short-range wireless network connection. The short-range network connection may utilize an ultra-low power wireless communication protocol.

The gateway device may further comprise a data storage component. The collected data may be buffered in the data storage component prior to providing the collected data to the study coordinating system over the first network connection. Buffering the collected data in the data storage component may be performed responsive to detecting disruption of the first network connection. Detecting disruption of the first network connection may comprise determining that the first network connection is at least one of unavailable, intermittent, and experiencing reduced available bandwidth.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A gateway device comprising:
   at least one processing device comprising a processor coupled to a memory;
   at least one network interface; and
   at least one sensor device interconnect;
   the at least one processing device being configured:
   to pair one or more sensor devices of a body area network associated with a subject with the gateway device utilizing the at least one sensor device interconnect, wherein pairing the one or more sensor devices comprises identifying sensing capabilities of the one or more sensor devices;
   to provide, to a study coordinating system over a first network connection established utilizing the at least one network interface, a gateway identifier for the gateway device and information characterizing the identified sensing capabilities of the one or more sensor devices paired with the gateway device;
   to receive, from the study coordinating system over the first network connection, one or more study parameters for at least one study to be conducted involving the subject, the one or more study parameters identifying data to be collected from at least one of the one or more sensor devices paired with the gateway device;
   to collect the identified data from the at least one sensor device paired with the gateway device over a second network connection established utilizing the at least one network interface; and
   to provide the collected data to the study coordinating system over the first network connection,
   wherein pairing a given one of the one or more sensor devices of the body area network with the gateway device is based at least in part on one or more signals received from the given sensor device characterizing an electric field generated in a vicinity of the at least one sensor device interconnect.

2. The gateway device of claim 1, wherein the first network connection comprises a long-range wireless network connection and the second network connection comprises a short-range wireless network connection.

3. The gateway device of claim 2, wherein the short-range network connection utilizes an ultra-low power wireless communication protocol.

4. The gateway device of claim 1, wherein the at least one sensor device interconnect comprises a physical mount for attaching a given sensor device to the gateway device.

5. The gateway device of claim 4, wherein the physical mount comprises a magnetic interconnect for attaching the given sensor device to the gateway device.

6. The gateway device of claim 1, wherein the at least one sensor device interconnect comprises one or more inductive coils configured to charge a given one of the one or more sensor devices when the given sensor device is in close physical proximity to the at least one sensor device interconnect.

7. The gateway device of claim 1, wherein the at least one sensor device interconnect comprises one or more photodetectors and transmitters configured for high-speed data transfer with a given one of the one or more sensor devices when aligned with corresponding photodetectors and transmitters of the given sensor device.

8. The gateway device of claim 1, wherein the at least one sensor device interconnect comprises one or more signal generators configured to generate the electric field in the vicinity of the at least one sensor device interconnect.

9. The gateway device of claim 1, wherein pairing the given sensor device comprises parsing the one or more signals received from the given sensor device to confirm placement and identification of the given sensor device relative to the at least one sensor device interconnect.

10. The gateway device of claim 1, wherein pairing the given sensor device with the gateway device comprises identifying configuration parameters for the given sensor device and generating a configuration signal comprising the identified configuration parameters for delivery to the given sensor device utilizing the one or more signal generators.

11. The gateway device of claim 10, wherein the identified configuration parameters comprise at least one of one or more programming data commands, one or more configuration commands, one or more unique identifiers, and one or more sensor calibration signals.

12. The gateway device of claim 1, wherein the gateway identifier for the gateway device comprises at least one of a bar code, a quick response code, and a radio frequency identifier.

13. The gateway device of claim 1, further comprising a data storage component, the at least one processing device being further configured to buffer the collected data in the data storage component prior to providing the collected data to the study coordinating system over the first network connection.

14. The gateway device of claim 13, wherein buffering the collected data in the data storage component is performed responsive to detecting disruption of the first network connection.

15. The gateway device of claim 14, wherein detecting disruption of the first network connection comprises determining that the first network connection is at least one of unavailable, intermittent, and experiencing reduced available bandwidth.

16. The gateway device of claim 1, wherein the at least one processing device is further configured to apply at least one of compression and encryption to the collected data prior to providing the collected data to the study coordinating system over the first network connection.

17. The gateway device of claim 1, wherein the one or more study parameters received from the study coordinating system further identify stimulus to be applied to the subject as part of the at least one study, and wherein the at least one processing device is further configured to provide one or more commands to initiate application of stimulus to the subject over the second network connection to at least one stimulating device paired with the gateway device.

18. The gateway device of claim 17, wherein the at least one stimulating device comprises at least one of the one or more sensor devices.

19. A computer program product comprising a non-transitory processor-readable storage medium having stored therein executable program code which, when executed, causes at least one processing device of a gateway device:
to pair one or more sensor devices of a body area network associated with a subject with the gateway device utilizing at least one sensor device interconnect of the gateway device, wherein pairing the one or more sensor devices comprises identifying sensing capabilities of the one or more sensor devices;
to provide, to a study coordinating system over a first network connection established utilizing at least one network interface of the gateway device, a gateway identifier for the gateway device and information characterizing the identified sensing capabilities of the one or more sensor devices paired with the gateway device;
to receive, from the study coordinating system over the first network connection, one or more study parameters for at least one study to be conducted involving the subject, the one or more study parameters identifying data to be collected from at least one of the one or more sensor devices paired with the gateway device;
to collect the identified data from the at least one sensor device paired with the gateway device over a second network connection established utilizing the at least one network interface; and
to provide the collected data to the study coordinating system over the first network connection,
wherein pairing a given one of the one or more sensor devices of the body area network with the gateway device is based at least in part on one or more signals received from the given sensor device characterizing an electric field generated in a vicinity of the at least one sensor device interconnect.

20. A method comprising:
pairing one or more sensor devices of a body area network associated with a subject with a gateway device utilizing at least one sensor device interconnect of the gateway device, wherein pairing the one or more sensor devices comprises identifying sensing capabilities of the one or more sensor devices;
providing, to a study coordinating system over a first network connection established utilizing at least one network interface of the gateway device, a gateway identifier for the gateway device and information characterizing the identified sensing capabilities of the one or more sensor devices paired with the gateway device;
receiving, from the study coordinating system over the first network connection, one or more study parameters for at least one study to be conducted involving the subject, the one or more study parameters identifying data to be collected from at least one of the one or more sensor devices paired with the gateway device;
collecting the identified data from the at least one sensor device paired with the gateway device over a second network connection established utilizing the at least one network interface; and
providing the collected data to the study coordinating system over the first network connection;
wherein pairing a given one of the one or more sensor devices of the body area network with the gateway device is based at least in part on one or more signals received from the given sensor device characterizing an electric field generated in a vicinity of the at least one sensor device interconnect; and
wherein the method is performed by at least one processing device comprising a processor coupled to a memory.

* * * * *